United States Patent [19]

Summers et al.

[11] Patent Number: 5,120,749
[45] Date of Patent: Jun. 9, 1992

[54] PLATELET ACTIVATING ANTAGONISTS

[75] Inventors: James B. Summers, Libertyville; George S. Sheppard, Wilmette; James G. Phillips, Antioch; Daisy Pireh, Lincolnshire; Douglas H. Steinman, Morton Grove, all of Ill.; Paul D. May, Bristol, Wis.

[73] Assignee: Abbott Laboratories, Abbott Park, Ill.

[21] Appl. No.: 658,134

[22] Filed: Feb. 20, 1991

[51] Int. Cl.$^5$ .................. C07D 403/14; C07D 401/14; A61K 31/40
[52] U.S. Cl. .................................... 514/337; 546/273; 546/184
[58] Field of Search ............... 514/336, 342, 343, 337; 546/280, 281, 284, 273

[56] References Cited

U.S. PATENT DOCUMENTS

| | | | |
|---|---|---|---|
| 4,273,782 | 6/1981 | Cross et al. | 546/273 X |
| 4,786,645 | 11/1988 | Fabre et al. | 514/333 |
| 4,948,795 | 8/1990 | Mase et al. | 514/252 |

FOREIGN PATENT DOCUMENTS 0279681  8/1988  European Pat. Off. ............ 546/270

Primary Examiner—Alan L. Rotman
Assistant Examiner—Barbara Schmidt Twordzik
Attorney, Agent, or Firm—Jerry F. Janssen

[57] ABSTRACT

Indole compounds substituted at the 1- or 3 position by a (pyrid-3 yl)thiazolid-4-yl)alkyl-, (pyrid-3-yl)thiazolid-4-oyl)-, (pyrid-3-yl)dithiolan-4-yl)alkyl- or (pyrid-3-yl)dithiolan-4-ol)- group are potent inhibitors of PAF and are useful in the treatment of PAF-related disorders including anaphylactic shock, respiratory distress syndrome, acute inflammation, delayed cellular immunity, parturtition, fetal lung maturation, and cellular differentiation.

8 Claims, No Drawings

PLATELET ACTIVATING ANTAGONISTS

TECHNICAL FIELD

This invention relates to compounds having pharmacological activity, to compositions containing these compounds, and to a medical method of treatment employing the compounds and compositions. More particularly, this invention concerns certain pyridylthiazolidine compounds and their salts which have platelet activating factor (PAF) antagonist activity, to pharmaceutical compositions containing these compounds, and to a method of treating PAF-mediated disorders.

BACKGROUND OF THE INVENTION

Platelet activating factor (PAF) is a phospholipid released from human and other animal cells and is an acetylglyceryl ether of phosphorylcholine as represented by the following formula:

$$\begin{array}{c} CH_2O(CH_2)_nCH_3 \\ | \\ CH_3COO-CH \quad O \\ | \quad \quad \| \\ CH_2O-P-O(CH_2)_2-N^+(CH_3)_3 \\ | \\ O^- \end{array}$$

where n is 15 or 17.

PAF is physiologically active and causes contraction of the airway smooth muscle, increased vascular permeability, platelet aggregation, hypotension and the like. It is now recognized as a powerful mediator of inflammation and may play a physiological or pathobiologic role in a variety of clinical conditions, such as asthma and pulmonary dysfunction, acute inflammation, transplanted organ rejection, endotoxin and IgG-induced shock, thrombosis, cardiac anaphylaxis, gastrointestinal ulceration, allergic skin diseases, retinal and corneal diseases, chemically induced liver cirrhosis, and ovimplantation in pregnancy.

Several anti-PAF agonists have been reported (e.g., U.S. Pat. No. 4,948,795, European Patent Application EP 279681, and U.S. Pat. No. 4,786,645) but none have received wide acceptance. Therefore, there is a continuing need for the development of potent, orally active antagonists of PAF which have low toxicity.

SUMMARY OF THE INVENTION

The present invention provides, in its principal aspect, compounds having PAF antagonist activity of the formula:

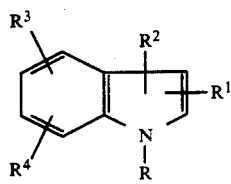

where R is B where B is

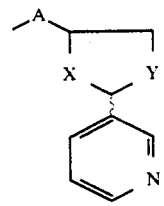

in which A is methylene or carbonyl, X is sulfur, or $NR^5$ where $R^5$ is hydrogen, alkyl of from one to six carbon atoms, alkoyl of from one to six carbon atoms, alkylsulfonyl of from one to six carbon atoms, or $-C(O)NR^6R^7$ where $R^6$ and $R^7$ are independently selected from hydrogen and alkyl of from one to six carbon atoms. The group Y is sulfur or methylene.

Alternatively, R is selected from (a) hydrogen; (b) alkyl of from one to six carbon atoms; (c) $-C(O)NR^6R^7$ where $R^6$ and $R^7$ are as previously defined; (d) $-C(O)OR^8$ where $R^8$ is alkyl of from one to six carbon atoms, phenyl, optionally substituted with alkyl of from one to six carbon atoms, alkoxy of from one to six carbon atoms, or halogen; phenylalkyl in which the alkyl portion contains from one to four carbon atoms, and phenylalkyl optionally substituted with alkyl of from one to six carbon atoms, alkoxy of from one to six carbon atoms, or halogen; (e) $-C(O)R^9$ where $R^9$ is hydrogen or alkyl of from one to six carbon atoms; (f) alkylsulfonyl of from one to six carbon atoms; (g) phenylsulfonyl, optionally substituted with alkyl of from one to six carbon atoms; (h) phenylalkyl in which the alkyl portion contains from one to six carbon atoms; and (i) benzoyl, optionally substituted with halogen, alkyl of from one to six carbon atoms, or alkoxy of from one to six carbon atoms.

$R^1$ is hydrogen or B with the proviso that one of R or $R^1$ is B, but R and $R^1$ are not both B.

$R^2$ is selected from hydrogen or alkyl of from one to six carbon atoms.

$R^3$ and $R^4$ are independently selected from the group consisting of (a) hydrogen; (b) halogen; (c) alkyl of from one to six carbon atoms; (d) alkoxy of from one to six carbon atoms; (e) alkoyl of from one to six carbon atoms; (f) cyano; (g) phenylalkoxy in which the alkoxy portion contains from one to six carbon atoms; (h) phenoxy; and (i) benzoyl, optionally substituted with alkyl of from one to six carbon atoms, alkoxy of from one to six carbon atoms, or halogen.

The pharmaceutically acceptable salts, and individual stereoisomers of compounds of structural formula I above, as well as mixtures thereof, are also contemplated as falling within the scope of the present invention.

In another aspect, the present invention provides pharmaceutical compositions useful for the treatment of PAF-mediated disorders comprising a therapeutically effective amount of a compound of formula I above in combination with a pharmaceutically acceptable carrier.

In another aspect, the present invention provides a method of inhibiting PAF activity by administering to a host mammal in need of such treatment a PAF-inhibiting effective amount of a compound of structure I above.

In yet another aspect of the present invention, there is provided a method of treating PAF-mediated disorders including asthma, anaphylactic shock, respiratory distress syndrome, acute inflammation, delayed cellular immunity, parturition, fetal lung maturation, and cellular differentiation by administering to a host mammal in need of such treatment a therapeutically effective amount of a compound of structure I above.

DETAILED DESCRIPTION AND PREFERRED EMBODIMENTS

In one particular embodiment, compounds of the present invention are represented by formula II:

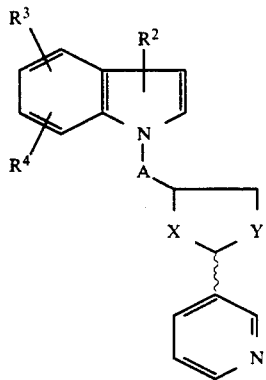

II where A, X, Y, $R^2$, $R^3$, and $R^4$ are as defined above.

Preferred compounds of formula II are those in which A is carbonyl, $R^2$ is hydrogen or alkyl of from one to six carbon atoms, and $R^3$ is hydrogen, halogen, or phenylalkoxy in which the alkoxy portion contains from one to six carbon atoms, and $R^4$ is hydrogen. Particularly preferred are compounds of formula II in which $R^2$ is hydrogen or methyl; $R^3$ is selected from hydrogen, 5-phenylalkoxy, or 5-halo; X is NH; $R^4$ is hydrogen; and Y is S.

In another embodiment, compounds of the present invention are represented by formula III:

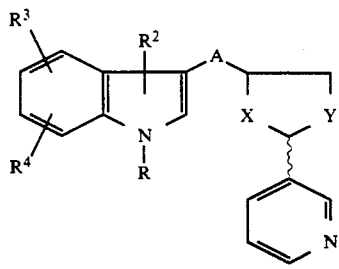

III where A, X, Y, R, $R^2$, $R^3$, and $R^4$ are as defined above.

Preferred compounds of formula III are those in which A is carbonyl, $R^2$ is hydrogen, R is selected from hydrogen, —C(O)N$R^6R^7$ (where $R^6R^7$ are as defined above), —C(O)O$R^8$ (where $R^8$ is as defined above), alkylphenylsulfonyl in which the alkyl portion contains from one to six carbon atoms, or phenylalkyl in which the alkyl portions contains from one to six carbon atoms; $R^3$ is hydrogen, alkyl of from one to six carbon atoms, or phenylalkoxy in which the alkoxy portion contains from one to six carbon atoms; and $R^4$ is hydrogen. Particularly preferred compounds of formula III are those in which R is hydrogen, —C(O)N(CH$_3$)$_2$, —C(O)N(CH$_2$CH$_3$)$_2$, or tert-butoxycarbonyl; $R^3$ is hydrogen, phenylmethoxy, or methyl; $R^2$ and $R^4$ is hydrogen; X is NH; and Y is S.

Examples of compounds contemplated as falling within the scope of the present invention include, but are not necessarily limited to:

1-[2-(3-pyridinyl)-thiazolid-4-oyl]indole;
1-[2-(3-pyridinyl)-thiazolid-4-oyl]-2,5-dimethylindole;
1-[2-(3-pyridinyl)-thiazolid-4-oyl]-4-chloroindole;
1-[2-(3-pyridinyl)-thiazolid-4-oyl]-4-bromoindole;
1-[2-(3-pyrindinyl)-thiazolid-4-oyl]-5-chloroindole;
1-[2-(3-pyridinyl)-thiazolid-4-oyl]-6-fluoroindole;
1-[2-(3-pyridinyl)-thiazolid-4-oyl]-6-chloroindole;
1-[2-(3-pyridinyl)-thiazolid-4-oyl]-6-bromoindole;
1-[2-(3-pyridinyl)-thiazolid-4-oyl]-5-cyanoindole;
1-[2-(3-pyridinyl)-thiazolid-4-oyl]-5,6-dimethoxyindole;
1-[2-(3-pyridinyl)thiazolid-4-oyl]-5-phenylmethoxyindole;
1-[2-(3-pyridinyl)thiazolid-4-oyl]-6-phenylmethoxyindole;
1-[2-(3-pyridinyl)-thiazolid-4-oyl]-4-benzoylindole;
1-[2-(3-pyridinyl)-thiazolid-4-oyl]-4-(3,4,5-trimethoxybenzoyl)indole;
1-[2-(3-pyridinyl)-thiazolid-4-oyl]-6-benzoylindole;
3-[2-(3-pyridinyl)-thiazolid-4-ylmethyl]indole;
3-[2-(3-pyridinyl)-thiazolid-4-oyl]indole;
1-methyl-3-[2-(3-pyridinyl)-thiazolid-4-oyl]indole;
2-methyl-3-[2-(3-pyridinyl)-thiazolid-4-oyl]indole;
7-methyl-3-[2-(3-pyridinyl)thiazolid-4-oyl]indole;
1,2-dimethyl-3-[2-(3-pyridinyl)-thiazolid-4-oyl]indole;
1-ethyl-3-[2-(3-pyridinyl)-thiazolid-4-oyl]indole;
1-pivaloyl-3-[2-(3-pyridinyl)-thiazolid-4-oyl]indole;
1-phenylmethyl-3-[2-(3-pyridinyl)-thiazolid-4-oyl]indole;
3-[2-(3-pyridinyl)thiazolid-4-oyl]-4-phenylmethoxyindole;
3-[2-(3-pyridinyl)thiazolid-4-oyl]-5-phenylmethoxyindole;
3-[2-(3-pyridinyl)thiazolid-4-oyl]-6-phenylmethoxyindole;
3-[2-(3-pryidinyl)thiazolid-4-oyl]-7-phenylmethoxyindole;
1-methylsulfonyl-3-[2-(3-pyridinyl)-thiazolid-4-oyl]indole;
1-iso-propylsulfonyl-3-[2-(3-pyridinyl)-thiazolid-4-oyl]indole;
1-phenylsulfonyl-3-[2-(3-pyridinyl)-thiazolid-4-oyl]indole;
1-(4-chlorobenzoyl)-3-[2-(3-pyridinyl)-thiazolid-4-oyl]indole;
1-tert-butoxycarbonyl-3-[2-(3-pyridinyl)-thiazolid-4-oyl]indole;
1-tert-butoxycarbonyl-6-phenylmethoxy-3-[2-(3-pyridinyl)-thiazolid-4-oyl]indole;
1-tert-butoxycarbonyl-2-methyl-3-[2-(3-pyridinyl)-thiazolid-4-oyl]indole;
1-ethoxycarbonyl-3-[2-(3-pyridinyl)-thiazolid-4-oyl]indole;
1-methoxycarbonyl-3-[2-(3-pyridinyl)-thiazolid-4-oyl]indole;
1-tert-butoxycarbonyl-7-phenylmethoxy-3-[2-(3-pyridinyl)-thiazolid-4-oyl]indole;
1-tert-butoxycarbonyl-3-[2-(3-pyridinyl)-3-formylcarbonylthiazolid-4-oyl]indole;
1-tert-butoxycarbonyl-3-[2-(3-pyridinyl)-3-acetylthiazolid-4-oyl]indole;
1-tert-butoxycarbonyl-3-[2-(3-pyridinyl)-3-acetylthiazolid-4-oyl]indole;

1-phenylmethoxycarbonyl-3-[2-(3-pyridinyl)-thiazolid-4-oyl]indole;
1-(N,N-dimethylcarbamoyl)-3-[2-(3-pyridinyl)-thiazolid-4-oyl]indole;
1-(N,N-diethylcarbamoyl)-3-[2-(3-pyridinyl)-thaizolid-4-oyl]indole;
1-(N,N-dimethylcarbamoyl)-7-phenylmethoxy-3-[2-(3-pyridinyl)-thiazolid-4-oyl]indole;
1-(N,N-dimethylcarbamoyl)-6-phenylmethoxy-3-[2-(3-pyridinyl)-thiazolid-4-oyl]indole;
1-(N-tert-butoxycarbamoyl)-3-[2-(3-pyridinyl)-thiazolid-4-oyl]indole;
1-(1-morpholinocarbonyl)-3-[2-(3-pyridinyl)-thiazolid-4-oyl]indole;
1-[2-(3-pyridinyl)-dithiolan-4-oyl]indole;
3-[2-(3-pyridinyl)-dithiolan-4-oyl]indole;
1-phenylsulfonyl 3-[2-(3-pyridinyl)-dithiolan-4-oyl]indole;
cis-1-tert-butoxycarbonyl-3-[2-(3-pyridinyl)-dithiolan-4-oyl]indole;
trans-1-tert-butoxycarbonyl-3-[2-(3-pyridinyl)-dithiolan-4-oyl]indole;
1-(N-methyl, N-phenylcarbamoyl)-3-[2-(3-pyridinyl)-thiazolid-4-oyl]indole;
and the pharmaceutically acceptable salts thereof.

As used throughout this specification and the appended claims, the following terms have the meanings ascribed to them:

The term "carbamoyl" refers to a structure of formula —CONR$^6$R$^7$ wherein R$^6$ and R$^7$ are independently selected from hydrogen or a straight or branched alkyl radical of from one to six carbon atoms. Representative examples of carbamoyl groups, include —C(O)NH$_2$, N,N-dimethylcarbamoyl, N-tert-butylcarbamoyl, N-methyl-N-ethylcarbamoyl and the like.

The term "carboalkoxy" as used herein refers to a structure of formula —C(O)OR$^8$ wherein R$^8$ is a straight or branched alkyl radical of from one to six carbon atoms, phenyl or substituted phenyl. Representative examples of carboalkoxy groups include carbomethoxy, carboethoxy, carbo(iso-propoxy), carbobutoxy, carbo(sec-butoxy), carbo(iso-butoxy), carbo(tert-butoxy), phenoxycarbonyl, and the like.

The term "alkoxyl" as used herein refers to formyl and radicals of the structure —C(O)—alkyl in which the alkyl portion is a straight or branched alkyl group of from one to six carbon atoms. Representative examples of alkoyl groups include formyl, acetyl, propionyl, butyryl, isobutyryl, pivaloyl, and the like.

The term "alkoxy" as used herein refers to a lower alkyl group, as defined herein, which is bonded to the parent molecular moiety through an oxygen atom Representative examples of alkoxy groups include methoxy, ethoxy, t-butoxy, and the like.

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "alkylsufonyl" is used herein to mean —SO$_2$(alkyl) where the alkyl group is as defined above. Representative examples of lower alkylsufonyl groups include methylsulfonyl, ethylsufonyl, isopropylsulfonyl and the like.

The terms "PAF-related disorders" and "PAF-mediated disorders" are used herein to mean disorders related to PAF or mediated by PAF, including asthma, anaphylactic shock, respiratory distress syndromes, acute inflammation delayed cellular immunity, parturition, fetal lung maturation, and cellular differentiation.

The term "phenylalkoxy" is used herein to mean an phenyl group appended to an alkoxy radical as previously defined. Representative examples of phenylakoxy groups include phenylmethoxy (i.e. benzyloxy), 1-phenylethoxy, 2-phenylethoxy, 2-phenylpropoxy, and the like.

The term "pharmaceutically acceptable salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. (See, for example S. M. Berge, et al., "Pharmaceutical Salts," *J. Pharm. Sci.*, 66: 1-19 (1977) which is incorporated herein by reference.)

Individual enantiomeric forms of compounds of the present invention can be separated from mixtures thereof by techniques well known in the art. For example, a mixture of diastereomeric salts may be formed by reacting the compounds of the present invention with a optically pure form of an acid, followed by purification of the mixture of diastereomers by recrystallization or chromatography and subsequent recovery of the resolved compound from the salt by basification. Alternatively, the optical isomers of the compounds of the present invention can be separated from one another by chromatographic techniques employing separation on an optically active chromatographic medium.

The present invention also provides pharmaceutical compositions which comprise one or more of the compounds of formula 1 above formulated together with one or more nontoxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as perservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium sterate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredients(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum methydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.001 to about 100, more preferably of about 0.01 to about 20, and most preferably about 0.1 to about 10 mg of active compound per kilogram of body weight per day are administered orally to a mammalian patient. If desired, the effective daily dose may be divided into multiple doses for purposes of administration, e.g. two to four separate doses per day.

In general, the compounds of this invention are synthesized by reaction schemes I though XII as illustrated below. It should be understood that that X, Y, A, $R_1$, and $R_2$ as used herein correspond to the groups identified by Formula I.

The compounds of Formula (I) may be prepared using the reactions and techniques described in this section. The reactions are performed in a solvent appropriate to the reagents and materials employed and suitable for the transformation being effected. It is understood by those skilled in the art of organic synthesis that the functionality present on the heterocycle and other portions of the molecule must be consistent with the chemical transformation proposed. This will frequently necessitate judgement as to the order of synthetic steps, protecting groups required and deprotection conditions.

Scheme I

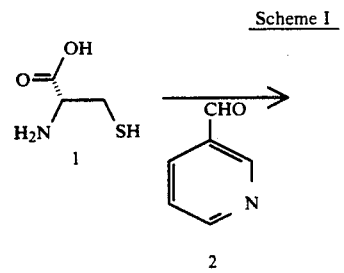

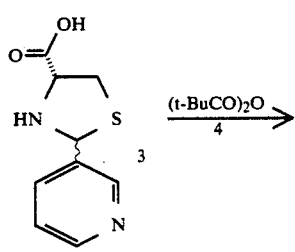

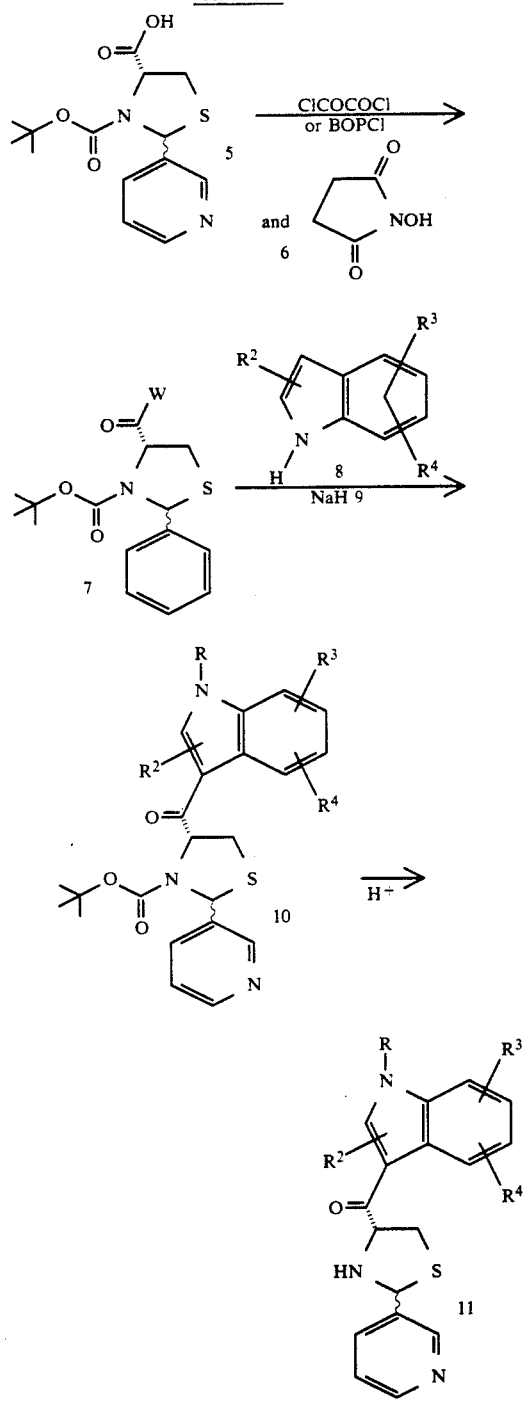

SCHEME I

According to the foregoing reaction scheme I, L-cysteine (1) is condensed with 3-pyridine aldehyde (2) to produce 2-(3-pyridinyl)-4-thiazolidinecarboxylic acid (3). The thiazolidine nitrogen is protected with an appropriate group, preferably carbo-tert-butoxy (BOC) with di-tert-butyl dicarbonate (4). The resulting 2-(3-pyridinyl)-3-tert-butoxycarbonyl-4-thiazolidinecarboxylic acid (5) is converted to an active ester (7), preferably the acid chloride (W is Cl), through the action of oxalyl chloride, or the N-hydroxysuccinimide ester (W is O-succinimide) through the action of N-hydroxylsuccinimide and a coupling agent such as dicyclohexylcarbodiimide or bis (2-oxo-3-oxazolidinyl)phosphinic chloride. The anion of an unsubstituted or substituted indole (8) is prepared by the reaction of the indole with a strong base, preferably sodium hydride (9) and the this anion is reacted with the active ester (7) to give the 1-[2-(3-pyridinyl)-3-tert-butoxycarbonyl-thiaz-4-oyl]indole (10). The BOC protecting group can be removed with acid, preferably HCl, to the produce 1-[2-(3-pyridinyl)-thiazolid-4-oyl]indole (11).

SCHEME II

According to the foregoing reaction scheme II, 2-(3-pyridinyl)-3-tert-butoxycarbonyl-4-thiazolidinecarboxylic acid (5) is converted to the acid chloride (7), preferably by treatment with oxalyl chloride or thionyl chloride. Alternatively the acid (5) may first be converted to its salt by treatment with a base, such as sodium hydride, and then treated with oxalyl chloride or thionyl chloride to afford 7. Reaction of the acid chloride (7) with a lewis acid, preferably aluminum chloride, followed by an unsubstituted or substituted indole (8) yields the 3-[2-(3-pyridinyl)-3-tert-butoxycarbonyl-thiazolid-4-oyl]indole (12). The BOC group can be removed from 12 by treatment with an acid, preferably HCl.

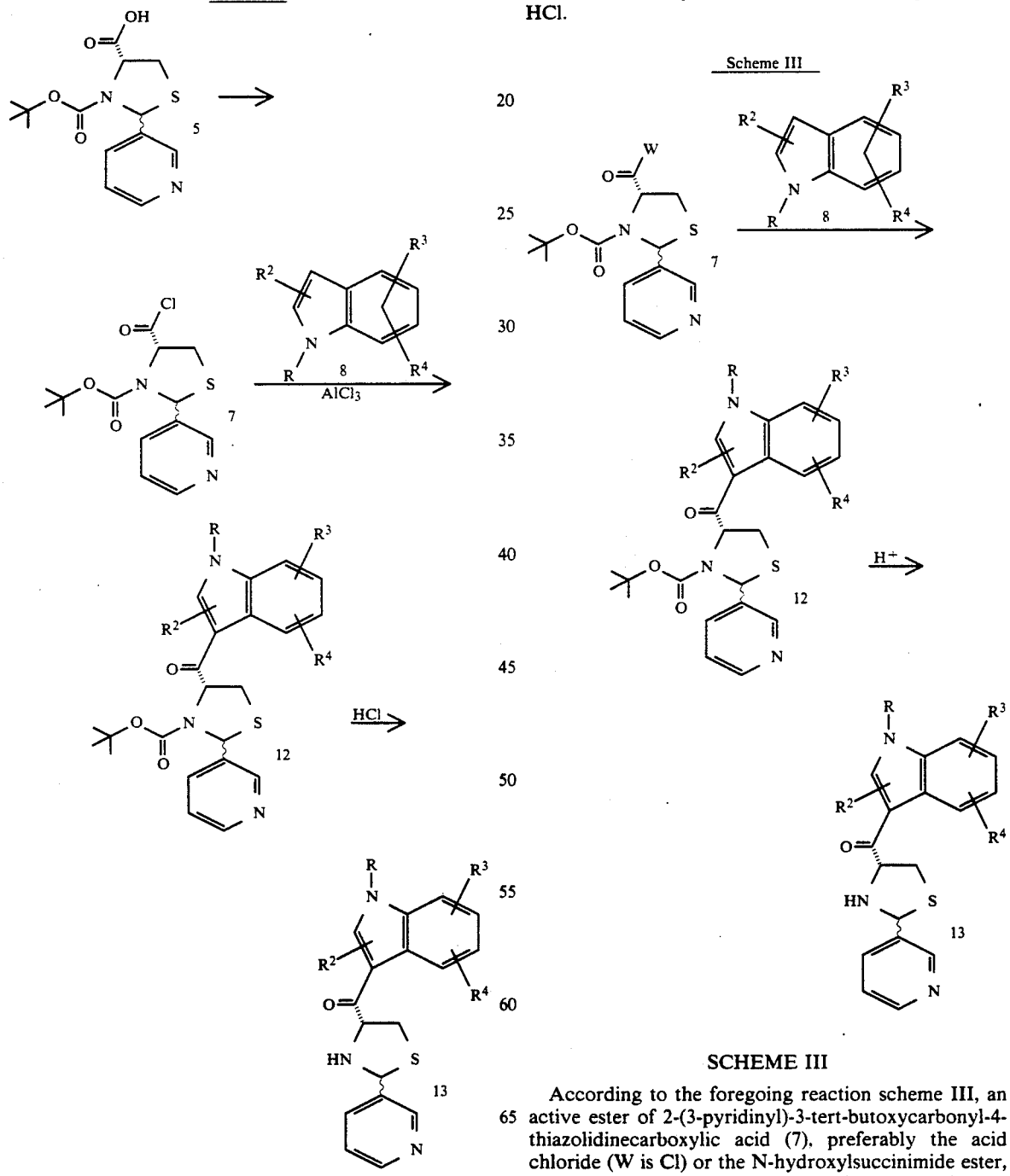

SCHEME III

According to the foregoing reaction scheme III, an active ester of 2-(3-pyridinyl)-3-tert-butoxycarbonyl-4-thiazolidinecarboxylic acid (7), preferably the acid chloride (W is Cl) or the N-hydroxylsuccinimide ester, prepared as described in scheme I, is treated with the anion of an unsubstituted or substituted indole (8) in a solvent, preferably benzene, to give a 3-[2-(3-pyridinyl)-3-tert-butoxycarbonylthiazolid-4-oyl]indole (12). The anion is prepared from the indole and a strong base, preferably ethyl magnesium bromide. The BOC group is removed from 12 by treatment with an acid, preferably HCl.

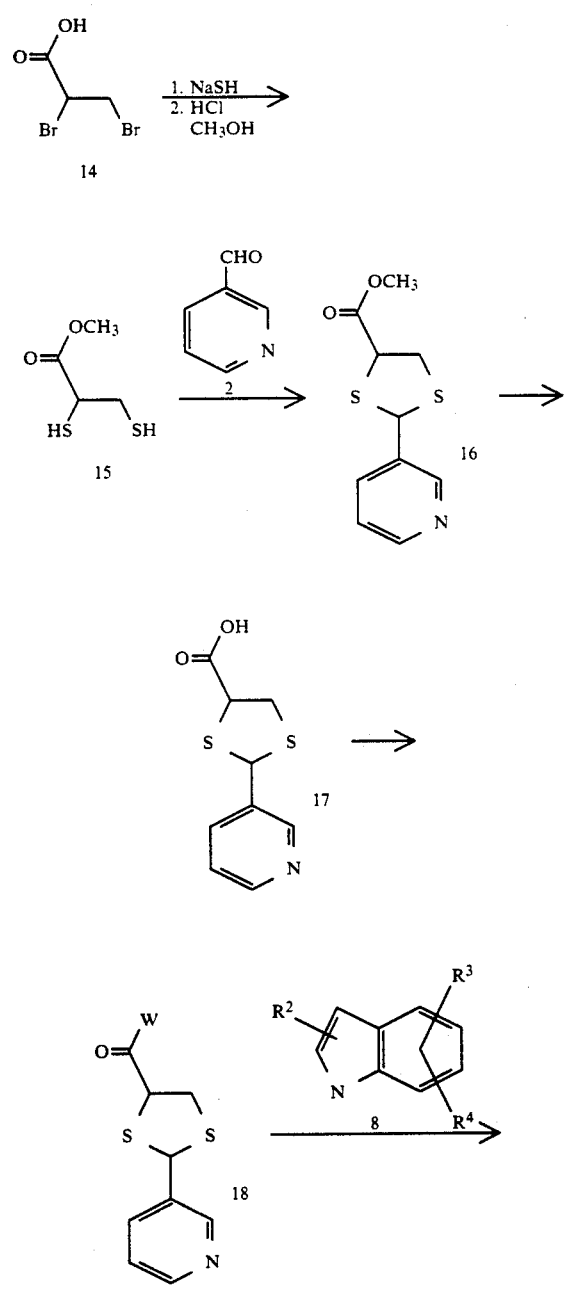

-continued
Scheme IV

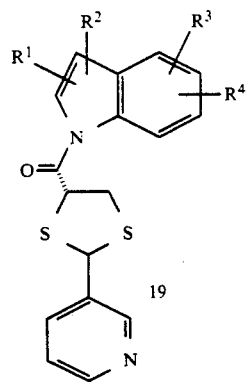

SCHEME IV

According to the foregoing reaction scheme IV, 2,3-dibromopropionic acid (14) is treated with NaSH followed by esterification with HCl in methanol to give methyl 2,3-dimercaptopropenonate (15). This dithiol (15) is condensed with 3-pyridine carboxaldehyde in the presence of an acid catalyst, preferably p-toluenesulfonic acid to afford methyl 2-(3-pyridinyl)-4-dithiolanecarboxylate (16). The dithiolane ester is hydrolyzed to the corresponding acid (17) by treatment with aqueous base, preferably lithium hydroxide. 2-(3-Pyridinyl)-4-dithiolanecarboxylic acid (17) is then converted to an active ester (18), preferably the imidazolide (W is 1-imidazole) by treatment with carbonyl diimidazole. The anion of an unsubstituted or substituted indole (8) is prepared by treatment with a strong base, preferably sodium hydride, and this is reacted with the active ester (18) to afford 1-[2-(3-pyridinyl)-dithiolan-4-oyl]indole (19).

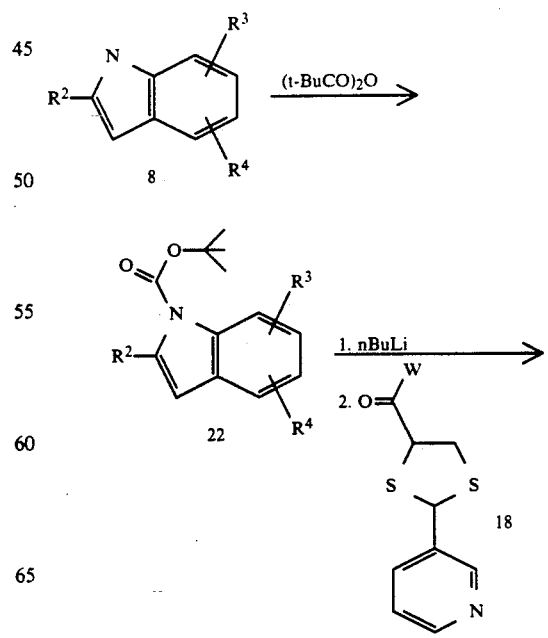

-continued
Scheme V

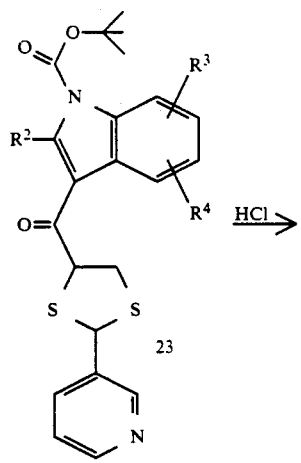

HCl →

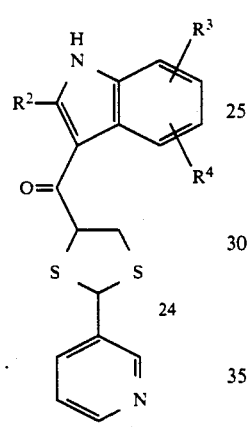

SCHEME V

According to the foregoing reaction scheme V, an indole without a nitrogen substituent is protected, preferably as the BOC from treating with di-tert-butyl dicarbonate (4), to give 22. This protected indole (22) is treated with a strong base, preferably n-butyl lithium, at −78° C., and then reacted with the active ester 18, preferably the N-methyl-N-methoxy amide (W is N(CH₃)OCH₃) to afford the 1-tert-butoxycarbonyl-3-[2-(3-pyridinyl)-dithiolan -4-oyl]indole (23). The BOC can be removed by treatment with an acid, preferably HCl to afford 3-[2-(3-pyridinyl)-dithiolan-4-oyl]indole (24).

Scheme VI

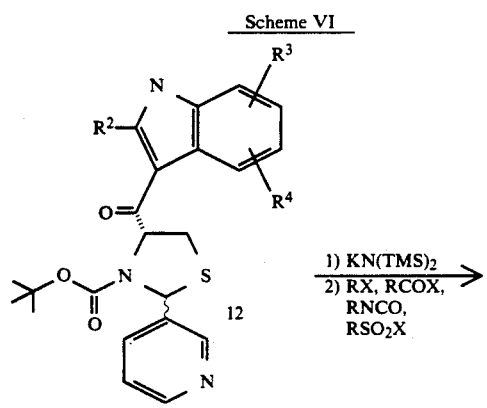

-continued
Scheme VI

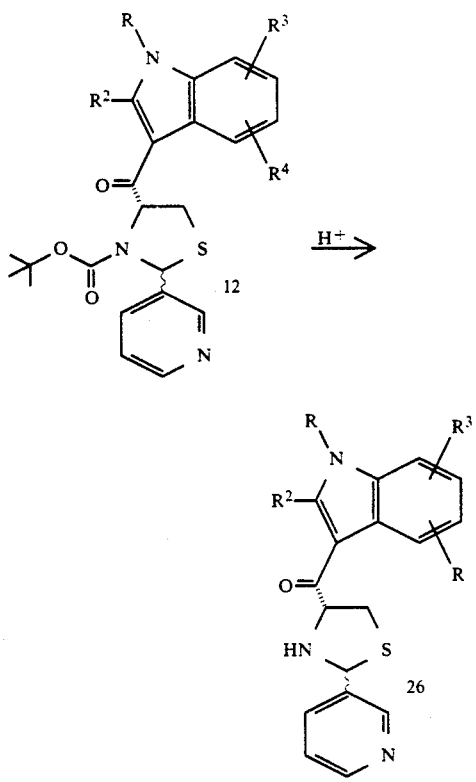

SCHEME VI

According to the foregoing reaction scheme VI, a 3-[2-(3-pyridinyl)-3-tert-butoxycarbonylthiazolid-4-oyl-]indole (12) without a substituent on the indole nitrogen is treated with a strong base, preferably potassium hexamethyl disilazide, followed by treatment with an alkyl halide (RX) or an active ester (RCOX), such as an acid chloride, an isocyanate (RNCO), or an alkylsulfonyl halide (RSO₂X) to give the indole with a substituent on the indole nitrogen (25). The BOC group is removed from 20 by treatment with an acid, preferably HCl to afford 26.

Scheme VII

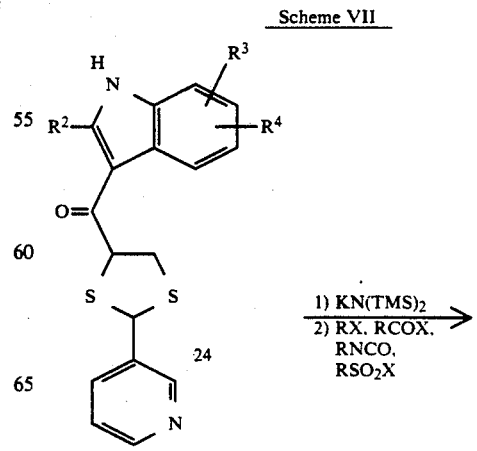

-continued
Scheme VII

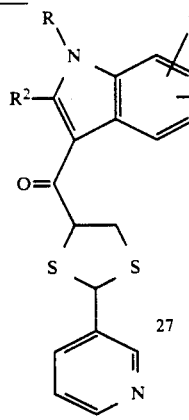

SCHEME VII

The foregoing reaction scheme VII describes transformations similar to scheme VI, except using the dithiolane 24 instead of the thiazolidine 12 to a afford 3-[2-(3-pyridinyl)-dithiolan-4-oyl]indole with a substituted indole nitrogen (27).

Scheme VIII

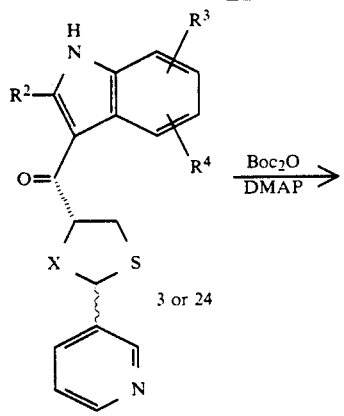

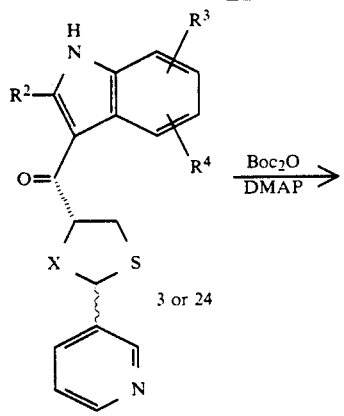

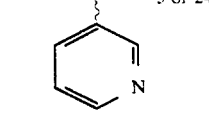

SCHEME VIII

According to the foregoing reaction scheme VIII, 3-[2-(3-pyridinyl)-dithiolan-4-oyl]indole with an unsubstituted indole nitrogen (3, X=NR³) or 3-[2-(3-pyridinyl)-thiazolid-4-oyl]indole with a substituted indole nitrogen (24, X=S) is treated with di-tert-butyl dicarbonate (4), preferably in the presence of an activating agent such as dimethylamino pyridine, to afford the BOC substituted compound 28.

Scheme IX

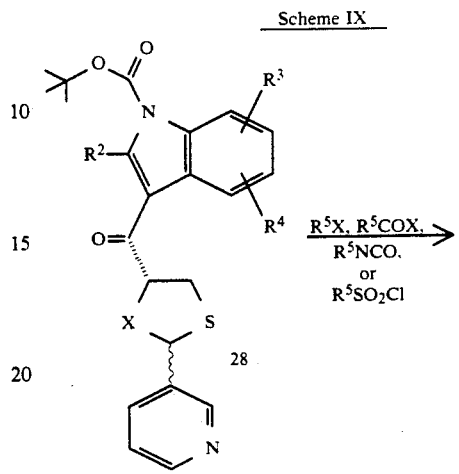

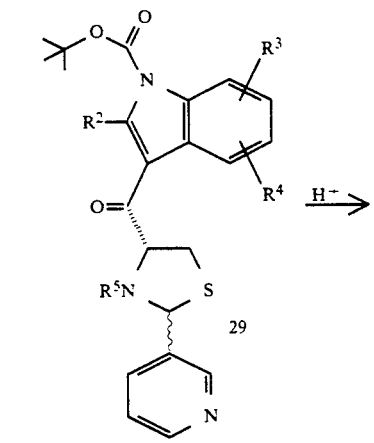

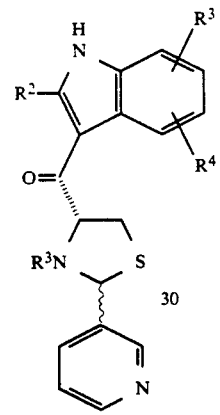

SCHEME IX

According to the foregoing reaction scheme IX, 1-tert-butoxycarbonyl-3-[2-(3-pyridinyl)-dithiolan-4-oyl]indole (28) is treated with a alkyl halide (RX), an alkoyl halide (RCOX), an isocyanante or an alkyl sulfonyl halide to afford the substituted compound 29 in the presence of a base such as triethylamine. The BOC group can be removed by treating with an acid, preferably HCl, to yield the substituted 3-[2-(3-pyridinyl)-dithiolan-4-oyl]indole 30).

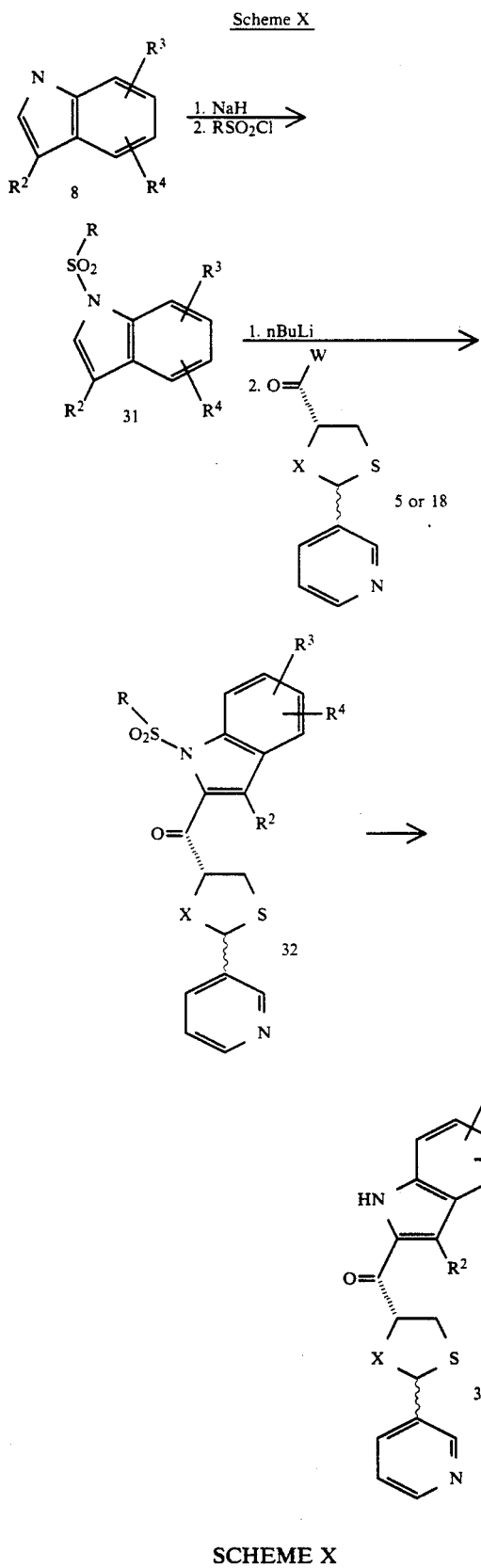

SCHEME X

According to the foregoing reaction scheme X, an unsubstituted or substituted indole is treated with a base, preferably sodium hydride and then reacted with an aryl sulfonyl chloride (ArSOCl$_2$), preferably benzenesulfonyl chloride to yield the sulfonyl indole 31. This compound (31) is then treated with n-butyl lithium followed by an active ester of 2-(3-pyridinyl)-3tert-butoxycarbonyl-4-thiazolidinecarboxylic acid (5, X is N-COtbutyl) or of 2-(3-pyridinyl)-4-dithiolanecarboxylic acid (18, X is S) to yield compound (32). The sulfonyl protecting group as well as other protecting groups can be remove by hydrolysis in aqueous base, preferably lithium hydroxide to afford a 2-[2-(3-pyridinyl)-thiazolid-4-oyl]indole or a 2-[2-(3-pyridinyl)-dithiolan-4-oyl]indole (30).

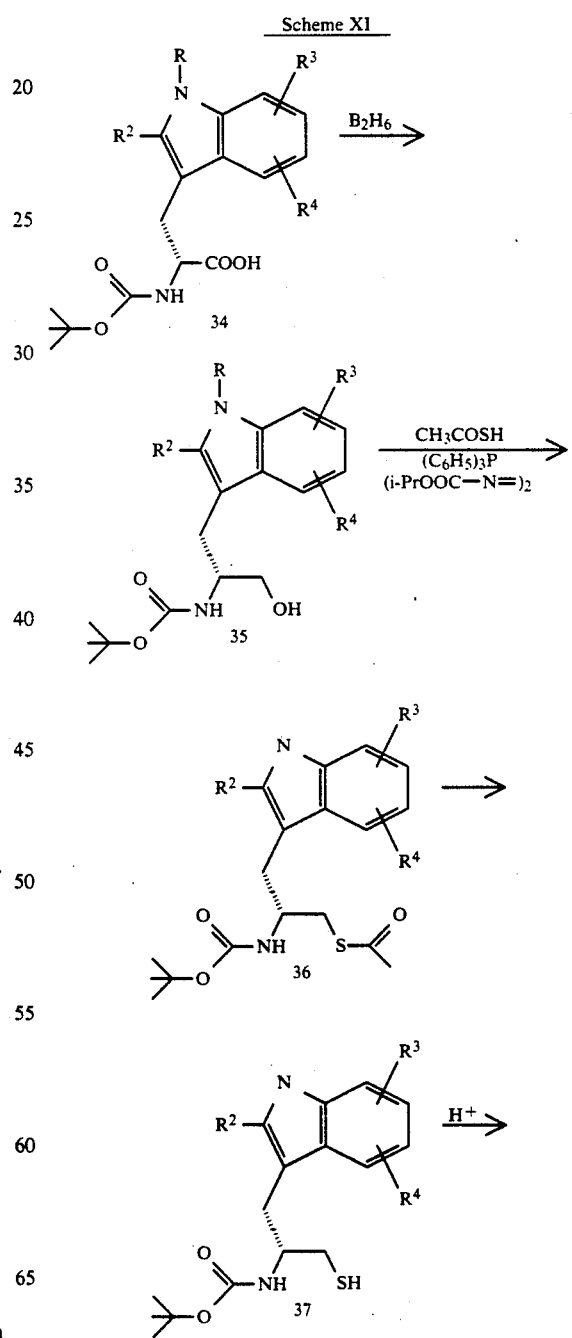

-continued
Scheme XI

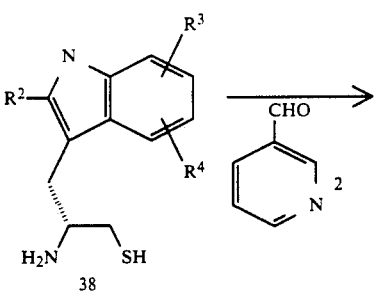

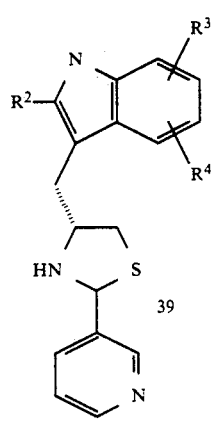

SCHEME XI

According to the foregoing reaction scheme XI, an unsubstituted or substituted BOC-D-tryptophan is reduced, preferably with diborane to yield a tryptanol (35). This compound (35) is treated with thioacetic acid, triphenyl phosphine, and a dialkylazodicarboxylate, preferably di-isopropyl azodicarboxylate to yield the thio acetate, 36. The thio ester (36) is hydrolyzed with hydroxide, preferably sodium hydroxide in methanol to yield a thiol, 37, and then the BOC group is cleaved with acid, preferably HCl, to yield an amino thiol, 38. This compound (38) is condensed with 3-pyridine carboxaldehyde to give a 3-[2-(3-pyridinyl)-thiazolid-4-oyl]methylindole (39).

Scheme XII

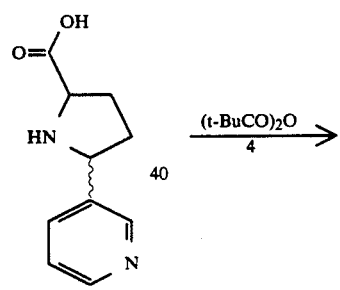

-continued
Scheme XII

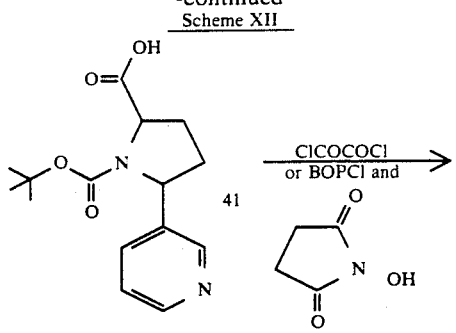

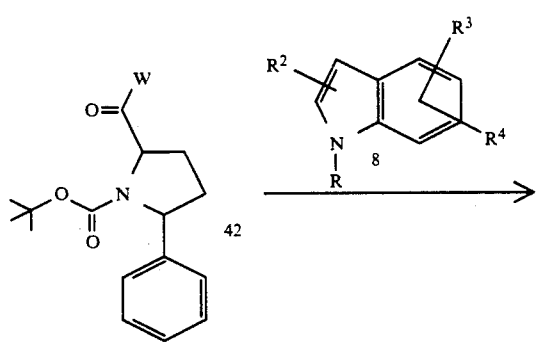

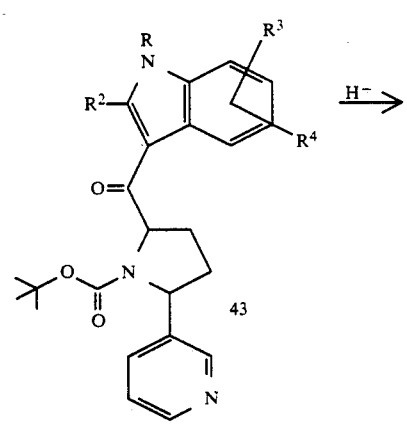

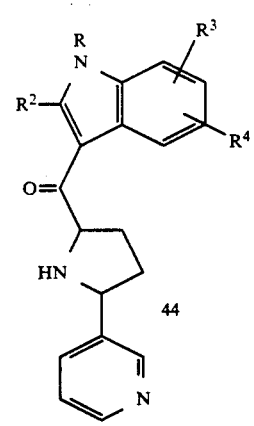

SCHEME XII

According to the foregoing reaction scheme XII, 2-(3-pyridinyl)-5-pyrrolidinecarboxylic acid (40) is protected with an appropriate group, preferably carbotertbutoxy (BOC) with di-tert-butyl dicarbonate (4). The resulting 1-tert-butoxycarbonyl-2-(3-pyridinyl)-5- thiazolidinecarboxylic acid (41) is converted to an active ester (7), preferably the acid chloride (W is Cl), through the action of oxalyl chloride, or the N-hydroxylsuccinimide ester (W is O-succinimide) through the action of N-hydroxylsuccinimide and a coupling agent such as dicyclohexylcarbodiimide or bis (2-oxo-3-oxazolidinyl)phosphinic chloride. The anion of an unsubstituted or substituted indole (8) is prepared by reacting the indole with a strong base, preferably ethyl magnesium bromide. The anion (8) is reacted with the active ester (42) to yield 3-[1-tert-butoxycarbonyl-2-(3-pyridinyl)-pyrrol-5-oyl]indole (43). The BOC group can be removed by treating 43 with an acid, preferably HCl yield 3-[2-(3-pyridinyl)-pyrrol-5-oyl]indole (43).

PAF INHIBITORY ACTIVITY OF THE COMPOUNDS OF THE PRESENT INVENTION

The ability of representative compounds of the present invention to inhibit PAF activity was determined in an in vitro test using the following method.

Citrated whole rabbit blood was obtained from Pel-Freez (Rogers, AR). Rabbit platelets were prepared by centrifugation and washing. The platelets were lysed by freeze-thawing and sonication; platelet membranes were prepared by centrifugation and washing. Final membrane preparations were stored frozen in 10 mM Tris/5 mM MgCl$_2$/2 mM EDTA (TME buffer, pH 7.0) with 0.25M sucrose added for membrane stabilization.

The standard PAF receptor binding assay contained 10 μg platelet membrane protein, 0.6 nM [$^3$H]C$_{18}$-PAF (from Amersham or New England Nuclear; specific activity 120-180 Ci/mmol), with and without test compound, in "binding buffer" consisting of TME with 0.25% bovine serum albumin added (Sigma, RIA grade). The final volume of the assay was 100 μl. The assay was conducted in Millititre-GV ™ (Millipore Corp.) filtration plates; incubation time was for 60 minutes at room temperature (22°-23° C.). "Specific binding" was operationally defined as the arithmetic difference between "total binding" of 0.6 nM [$^3$H]C$_{18}$-PAF (in the absence of added PAF) and "nonspecific binding" (in the presence of 1 μM PAF). After the prescribed incubation, platelet membranes were filtered under vacuum, and washed with 1 milliliter of "binding buffer". The filters were dried and removed. The bound radioactivity was quantitated with a Berthold TLC-Linear Analyzer model LB2842.

Dose-response curves of inhibition of specific [$^3$H]C$_{18}$-PAF binding by test compounds were conducted in triplicate, with at least four doses covering the active range. Experiments were repeated at least once. IC$_{50}$ values (concentration producing 50% inhibition) were determined by point-to-point evaluation. K$_i$ values of inhibitory binding constants were calculated according to the method of Cheng and Prusoff [*Biochem. Pharmacol.* 22 (1973) 3099-3108] whereby $$K_i = \frac{IC_{50}}{1 + ([[^3H]PAF]/K_d[^3H]PAF)}$$

$$= \frac{IC_{50}}{1 + (0.6\ nM/0.6\ nM)}$$

$$= \frac{IC_{50}}{2}$$

The values of K$_i$ for representative compounds of the present invention appear 8 in Table 1.

TABLE 1

| PAF Receptor Binding Activity | |
|---|---|
| Example | K$_i$ |
| 1 | 7 |
| 2 | 30 |
| 3 | 65 |
| 4 | 46 |
| 5 | 33 |
| 6 | 53 |
| 7 | 12 |
| 8 | 4 |
| 9 | 140 |
| 10 | 2100 |
| 11 | 15 |
| 12 | 15 |
| 13 | 2400 |
| 14 | 67 |
| 15 | 23 |
| 16 | 25 |
| 17 | 93 |
| 18 | 52 |
| 19 | 12,500 |
| 20 | 4 |
| 21 | 105 |
| 22 | 13 |
| 23 | 23 |
| 24 | 13 |
| 25 | 5 |
| 26 | 360 |
| 27 | 7 |
| 28 | 2 |
| 29 | 180 |
| 30 | 900 |
| 31 | 1700 |
| 32 | 1000 |
| 33 | 600 |
| 34 | 2 |
| 35 | 1 |
| 36 | 30 |
| 37 | 15 |
| 38 | 1 |
| 39 | 23 |
| 40 | 10 |
| 41 | 4 |
| 42 | 2 |
| 43 | 32 |
| 44 | 4 |
| 45 | 3 |
| 46 | 50 |
| 47 | 8 |
| 48 | 1 |
| 49 | 25 |
| 50 | 1 |
| 56 | 150 |
| 57 | 10,000 |
| 58 | 600 |

The foregoing may be better understood from the following Examples, which are presented for the purpose of illustration and not intended to limit the scope of the inventive concept.

EXAMPLE 1

Preparation of 1-(2-(3-pyridinyl)thiazolid-4-oyl)-5-phenylmethoxyindole

Step 1. 2-(3-pyridinyl)-4-thiazolidinecarboxylic acid

Cysteine (24.2 g, 0.2 mole) and 3-pyridine carboxaldehyde (21.4 g, 0.2 mmole) were suspended in 60% aqueous ethanol (400 mL) and the mixture was heated at 100° C. for 5 hours. The reaction mixture was then cooled and most of the solvent was removed in vacuo. The resulting slurry was washed with ethanol and filtered. This material was dried overnight in vacuo at 50° C. to afford the thiazolidine acid (34 g, 81%).

Step 2.
2-(3-pyridinyl)-3-tert-butoxycarbonyl-4-thiazolidinecarboxylic acid

To a slurry of 2-(3-pyridinyl)-4-thiazolidinecarboxylic acid (7.0 g, 33.3 mmol) as prepared in Step 1 in 40 mL dioxane was added 60 mL of 1M NaOH and di-tert-butyldicarbonate (1.5 eq, 50 mmol) in dioxane. The mixture was stirred for 19 h. The mixture was concentrated and the resulting liquid partitioned between ethyl acetate and water. The aqueous phase was extracted with ethyl acetate and dried to yield 2-(3-pyridinyl)-3-tert-butoxycarbonyl-4-thiazolidinecarboxylic acid (8.27 g, 80%)

Step 3.
2-(3-pyridinyl)-3-(tert-butoxycarbonyl)-4-thiazolidinecarboxylate N-hydroxysuccinimide ester.

2-(3-Pyridinyl)-3-tert-butoxycarbonyl-4-thiazolidinecarboxylic acid (20 g, 0.0644 mol), N-hydroxysuccinimide (8.14 g, 0.707 mol), and dimethylaminopyridine (787 mg, 0.0064 mol) were mixed and dimethylformamide (200 mL) added with stirring under $N_2$ atmosphere at room temperature. The flask was cooled and dicyclohexylcarbodiimide (13.2 g, 0.064 mol) added and the mixture stirred in an ice bath. The reaction mixture was then allowed to slowly warm to room temperature and stirred overnight. The mixture was concentrated under high vacuum, the residue extracted with ethyl acetate, and filtered. The material was chromatographed on a silica column to yield 2-(3-pyridinyl)-3-(tert-butoxycarbonyl)-4-thiazolidinecarboxylate N-hydroxysuccinimide ester. (16.99 g, 65%).

Step 4.
1-[2-(3-pyridinyl)-3-(tert-butoxycarbonyl)-4-thiazolid-4-oylmethyl]-5-phenylmethoxyindole.

Sodium hydride (60% dispersion, 147 mg, 0.00368 mol). tetrahydrofuran (3 mL), and dimethylsulfoxide (2 mL) were stirred under $N_2$ atmosphere and cooled in an ice bath. 5-Benzyloxyindole (822 mg, 0.00368 mol) in dimethylsulfoxide and tetrahydrofuran were added and the resulting suspension stirred at 0° C. until homogeneous and 2-(3-pyridinyl)-3-(tert-butoxycarbonyl)-4-thiazolidinecarboxylate N-hydroxysuccinimide ester (1.0 g, 0.00245 mol) added under $N_2$ atmosphere. The suspension was stirred at 0° C. for 15 min. and then allowed to warm to room temperature with stirring overnight. The reaction was quenched with 10% citric acid and the mixture diluted with ethyl acetate. The organic layer was washed and dried over magnesium sulfate and filtered. The filtrate was dissolved in dichloromethane and chromatographed on silica gel to yield 884 mg 1-[2-(3-pyridinyl)-3-(tert-butoxycarbonyl)-4-thiazid-4-oylmethyl]-5-phenylemthoxyindole (70%).

Step 5.
1-[2-(3-pyridinyl)-thiazolid-4-oyl]-5-phenylmethoxyindole

1-[2-(3-pyridinyl)-3-(tert-butoxycarbonyl)-4-thiazlid-4-oylmethyl]-5-phenylmethoxyindole (300 mg, 0.00058 mol) was stirred with dioxane under $N_2$ atmosphere. Hydrochloric acid/dioxane (2.5 mL, 4M, 0.01175 mol) was added and stirred at room temperature for 2 h. The reaction mixture was concentrated, azeotroped with toluene, and the solvent removed in vacuo. The residue was suspended in ether and washed with sodium bicarbonate. The organic phase was dried over $MgSO_4$ and the solvent evaporated to yield 1-[2-(3-pyridinyl)-thiazo-4-oyl]-5-phenylmethoxyindole (243.5 mg, 86%).

NMR (CDCl$_3$, 300 MHz) δ 3.08–3.19 (c, 1H), 3.23–3.33 (c, 1H), 3.47 (dd, ½H, J=3 Hz, 10.5 Hz), 3.59 (dd, ½H, J=3 Hz, 10.5 Hz), 4.55–4.69 (c, 1H), 5.12 (s, 2H), 5.70 (d, ½H, J=10.5 Hz), 6.01 (s, ½H), 6.61 (d, ½H, J=4.5 Hz), 6.68 (d, ½H, J=4.5 Hz), 7.05–7.15 (c, 2H), 7.28–7.51 (c, 7H), 7.87 (d, ½H, J=7.5 Hz), 7.95 (dt, ½H, J=7.5 Hz, 1.5 Hz), 8.48 (dd, 1H, J=4.5 Hz, 9 Hz), 8.53 (dd, ½H, J=3 Hz, 1.5 Hz), 8.62 (dd, ½H, J=3 Hz, 1.5 Hz).

Mass Spectrum (FAB): 416 (M+H)+.

EXAMPLE 2

Preparation of 1-[2-(3-pyridinyl)-thiazolid-4-oyl]indole dihydrochloride

Step 1. 1-[2-(3-pyridinyl)-thiazolid-4-oyl]indole

1-[2-(3-pyridinyl)-thiazolid-4-oyl]indole was prepared as described as described in Example 1, except indole was used instead of 5-phenylmethoxyindole.

Step 2. 1-[2-(3-pyridinyl)-thiazolid-4-oyl]indole dihydrochloride

The material prepared as in step 1 was dissolved in ether and treated with excess 4N HCl in dioxane. 1-[2-(3-pyridinyl)-thiazolid-4-oyl]indole dihydrochloride was isolated by filtration.

NMR (CDCl$_3$, 300 MHz): δ 8.84 (m, 1H), 8.66 (m, 1H), 8.50 (bd, 0.5H, J=5.2), 8.48 (bd, 0.5H, J=4.8), 7.97 (d, 0.5H, J=8.1), 7.90 (d, 0.5H, J=7.7), 7.58 (m, 1H), 7.54 (d, 0.5H, J=3.6), 7.45 (d, 0.5H, J=4.0), 7.35 (m, 3H), 6.76 (d, 0.5H, J=3.5), 6.70 (d, 0.5H, J=3.7), 6.03 (s, 0.5H), 5.72 (s, 0.5H), 4.67 (m, 1H), 3.62 (dd, 0.5H, J=6.9, 10.3), 3.49 (dd, 0.5H, J=6.9, 10.6), 3.30 (m, 1H).

Mass Spectrum (DCI/NH$_3$): 310 [(M+1)+, 100].

EXAMPLE 3

Preparation of 1-[2-(3-pyridinyl)-thiazolid-4-oyl]indole oxalate

1-[2-(3-pyridinyl)-thiazolid-4-oyl]indole, prepared as described in Example 2 above, was dissolved in ether and treated with excess oxalic acid in ether. The desired salt was isolated by filtration.

NMR (CDCl$_3$, 300 MHz): δ 8.84 (m, 1H), 8.66 (m, 1H), 8.50 (bd, 0.5H, J=5.2), 8.48 (bd, 0.5H, J=4.8), 7.97 (d, 0.5H, J=8.1), 7.90 (d, 0.5H, J=7.7), 7.58 (m, 1H), 7.54 (d, 0.5H, J=3.6), 7.45 (d, 0.5H, J=4.0), 7.35 (m, 3H), 6.76 (d, 0.5H, J=3.5), 6.70 (d, 0.5H, J=3.7), 6.03 (s, 0.5H), 5.72 (s, 0.5H), 4.67 (m, 1H), 3.62 (dd, 0.5H, J=6.9, 10.3), 3.49 (dd, 0.5H, J=6.9, 10.6), 3.30 (m, 1H).

Mass Spectrum (DCI/NH$_3$): 310 [M+1)+, 100].

EXAMPLE 4

Preparation of 1-[2-(3-pyridinyl)-thiazolid-4-oyl]-2,5-dimethylindole

1-[2-(3-pyridinyl)-thiazolid-4-oyl]-2,5-dimethylindole was prepared using the method of Example 1, except 2,5-dimethylindole was used instead of 5-phenylmethoxyindole.

NMR (CDCl$_3$, 300 MHz): δ 2.38 (s, 1-½H), 2.43 (s, 1-½H), 2.58 (s, 1-½H), 2.68 (s, 1-½H), 3.20-3.35 (c, 1H), 3.45-3.61 (c, 1H), 4.80 (t, 1H, J=7.5 Hz), 5.69 (s, ½H), 6.01 (s, ½H), 6.35 (s, ½H), 6.38 (s, ½H), 7.00 (d, ½H, J=9 Hz), 7.10 (d, ½H, J=9 Hz), 7.22–7.39 (c, 2H), 7.65 (d, ½H, J=9 Hz), 7.80 (d, ½H, J=9 Hz), 7.88 (dt, ½H, J=7.5 Hz, 1.5 Hz), 7.96 (dt, ½H,

J=7.5 Hz), 8.55 (dd, ½H, J=3 Hz), 1.5), 8.61 (dd, ½H, J=3 Hz, 1.5 Hz), 8.79 (d, ½H, J=3 Hz), 8.83 (d, ½H, J=3 Hz).

Mass Spectrum (DCI/NH$_3$): 338 (M+H)$^+$.

EXAMPLE 5

Preparation of
1-[2-(3-pyridinyl)-thiazolid-4-oyl]-4-chloroindole dihydrochloride 1-[2-(3-pyridinyl)-thiazolid-4-oyl]-4-chloroindole was prepared using the method of Example 1, except 4-chloroindole was used instead of 5-phenylmethoxyindole. The dihydrochloride salt was prepared as described in Example 2.

NMR (CDCl$_3$, 300 MHz): δ 3.3 (m), 3.45 (m), 3.6 (d, d, J=10 Hz, J=7 Hz, 3H), 4.6 (br s, 1H), 6.0 (br s, 1H), 5.8 (br s, 1H), 6.85 (d, 1H, 3 Hz), 6.9 (d, 3 Hz, 1H), 7.3 (m, 2H), 7.55 (d, 1H, J=3 Hz), 7.6 (d, 1H, J=3 Hz), 7.9 (d, 1H, J=3 Hz), 7.96 (m, 1H), 8.4 (d, d, 1H), 8.6 (dd, 1H, J=5 Hz), 8.63 (d, 1H, J=6 Hz), 8.8 (m, 1H).

EXAMPLE 6

Preparation of
1-[2-(3-pyridinyl)-thiazolid-4-oyl]-4-bromoindole dihydrochloride 1-[2-(3-pyridinyl)-thiazolid-4-oyl]-4-bromoindole was prepared using the method of Example 1, except 6-bromoindole was used instead of 5-phenylmethoxyindole. The dihydrochloride salt was prepared as described in Example 2.

NMR (CDCl$_3$, 300 MHz): δ 3.3 (m), 3.45 (m), 3.6 (dd, J=10 Hz, J=7 Hz, 3H), 4.6 (br s, 1H), 6.0 (br s, 1H), 5.8 (br s, 1H), 6.85 (d, 1H, 3 Hz), 6.9 (1H, d, 3 Hz), 7.3 (m, 2H), 7.55 (d, 1H, J=3 Hz), 7.6 (d, 1H, J=3 Hz), 7.9 (d, 1H, J=3 Hz), 7.96 (m, 1H), 8.4 (dd, 1H), 8.6 (dd, 1H, J=5 Hz), 8.63 (d, 1H, J=6 Hz), 8.8 (m, 1H).

EXAMPLE 7

Preparation of
1-[2-(3-pyridinyl)-thiazolid-4-oyl]-4-benzoylindole dihydrochloride 1-[2-(3-pyridinyl)-thiazolid-4-oyl]-4-benzoylindole was prepared using the method of Example 1, except 4-benzoylindole was used instead of 5-phenylmethoxyindole. The dihydrochloride salt was prepared as described in Example 2.

NMR (CDCl$_3$, 300 MHz): δ 8.83 (m, 1H), 8.74 (m, 1H), 8.64 (m, 0.5H), 8.57 (m, 0.5H), 7.96 (m, 0.5H), 7.88 (m, 0.5 H), 7.83 (m, 2H), 7.67 (d, J=3.7, 0.5H), 7.60 (m, 2.5H), 7.49 (m, 3H), 7.30 (m, 1H), 7.19 (d, J=4.4, 0.5H), 7.12 (d, J=3.7, 0.5H), 6.03 (m, 0.5H), 5.74 (m, 0.5H), 4.71 (m, 1H), 3.62 (dd, J=7.0, 10.4, 0.5H), 3.52 (dd, J=7.0, 10.6, 0.5H), 3.38 (m, 1H).

Mass Spectrum (DCI/NH$_3$): 414 (M+1+, 30), 239 (70), 222 (95), 124 (100).

EXAMPLE 8

Preparation of
1-[2-(3-pyridinyl)-thiazolid-4-oyl]-4-(3,4,5-trimethoxybenzoyl)indole 1-[2-(3-pyridinyl)-thiazolid-4-oyl]-4-(3,4,5-trimethoxybenzoyl)indole was prepared using the method of Example 1, except using 4-(3,4,5-trimethoxy)indole instead of 5-phenylmethoxyindole.

NMR (CDCl$_3$, 300 M Hz): δ 8.84 (bs, .5H), 8.81 (d, 0.5H, J=2.0 ), 8.74 (m, 1H), 8.62 (bd, 0.5H, J=3.3), 8.55 (bd, 0.5H, J=4.8), 7.92 (m, 1H), 7.68 (d, 0.5H, J=3.7), 7.64 (d, 0.5H, J=2.2), 7.60 (m, 1H), 7.47 (m, 1H), 7.36 (m, 1H), 7.11 (m, 3H), 6.01 (s, 0.5H), 5.72 (s, 0.5H), 4.72 (m, 1H), 3.96 (bs, 3H), 3.87 (s, 3H), 3.86 (s, 3H), 3.78 (m, 0.5H), 3.63 (m, 0.5H), 3.51 (dd, 0.5H, J=7.4, 10.7), 3.35 (dd, 0.5H, 7.3, 8.2).

Mass Spectrum (FAB): 504 (M+, 65), 195, 165 (100), 144.

EXAMPLE 9

Preparation of
1-[2-(3-pyridinyl)-thiazolid-4-oyl]-5-chloroindole dihydrochloride 1-[2-(3-pyridinyl)-thiazolid-4-oyl]-5-chloroindole was prepared using the method of Example 1, except 5-chloroindole was used instead of 5-phenylmethoxyindole. The dihydrochloride salt was prepared as described in Example 2.

NMR (CDCl$_3$, 300 MHz): δ 3.25 (dd, ½H, J=10.5 Hz, 10.5 Hz), 3.41–3.61 (c, 3½H), 5.10 (t, 1H, J=6 Hz), 5.99 (s, ½H), 6.19 (s, ½H), 6.79 (d, 1H, J=3 Hz), 7.35 (dd, ½H, J=9 Hz, 1.5 Hz), 7.41 (dd, ½H, J=9 Hz, 1.5 Hz), 7.73 (dd, 1H, J=6 Hz, 3 Hz), 7.90 (dd, ½H, 7.5 Hz, 3 Hz), 8.06 (dd, ½H, J=7.5 Hz, 3 Hz), 8.16 (d, ½H, J=3 Hz), 8.23 (d, ½H, J=3 Hz), 8.39 (d, 1H, J=9 Hz), 8.57 (d, ½H, J=7.5 Hz), 8.70 (d, ½H, J=7.5 Hz), 8.78 (d, ½H, J-4, 0.5 Hz), 8.86 (d, ½H, J=4.5 Hz), 8.93 (d, ½H, J=1.5 Hz), 9.01 (d, ½H, J=1.5 Hz)

EXAMPLE 10

Preparation of
1-[2-(3-pyridinyl)-thiazolid-4-oyl]-5-cyanoindole dihydrochloride 1-[2-(3-pyridinyl)-thiazolid-4-oyl]-5-cyanoindole was prepared using the method of Example 1, except 5-cyanoindole was used instead of 5-phenylmethoxyindole.

NMR (CDCl$_3$, 300 MHz): δ 3.23–3.29 (c, 1H), 3.32–3.49 (c, 1H), 5.07–5.15 (c, 1H), 5.95 (s, ½H) 6.10 (s, ½H), 7.12 (t, ½H, J=9 Hz), 7.21 (t, ½H, J=9 Hz), 7.53–7.84 (c, 2H), 7.93–8.03 (c, 1H), 8.16 (d, 1H, J=6 Hz), 8.22–8.32 (c, 1H), 8.49 (d, 1H, J=9 Hz), 8.61–8.76 (c, 1H), 8.79–8.98 (c, 1H).

EXAMPLE 11

Preparation of
1-(2-(3-pyridinyl)thiazolid-4-oyl)-5-phenylmethoxyindole dihydrochloride 1-(2-(3-pyridinyl)thiazolid-4-oyl)-5-phenylmethoxyindole was prepared using the method of Example 1. The dihydrochloride salt was prepared as described in Example 2.

NMR (CDCl$_3$, 300 MHz): δ 3.08–3.19 (c, 1H), 3.23–3.33 (c, 1H), 3.47 (dd, ½H, J=3 Hz, 10.5 Hz), 3.59 (dd, ½H, J=3 Hz, 10.5 Hz), 4.55–4.69 (c, 1H), 5.12 (s, 2H), 5.70 (d, ½H, J=10.5 Hz), 6.01 (s, ½H), 6.61 (d, ½H, J=4.5 Hz), 6.68 (d, ½H, J=4.5 Hz), 7.05–7.15 (c, 2H), 7.28–7.51 (c, 7H), 7.87 (d, ½H, J=7.5 Hz), 7.95 (dt, ½H, J=7.5 Hz, 1.5 Hz), 8.48 (dd, 1H, J=4.5 Hz, 9 Hz), 8.53 (dd, ½H, J=3 Hz, 1.5 Hz), 8.62 (dd, ½H, J=3 Hz, 1.5 Hz).

EXAMPLE 12

Preparation of
1-(2-(3-pyridinyl)thiazolid-4-oyl)-5-phenylmethoxyindole oxalate 1-(2-(3-pyridinyl)thiazolid-4-oyl)-5-phenylmethoxyindole was prepared using the method of Example 1. The salt was prepared as described in Example 3.

NMR (CDCl$_3$, 300 MHz): δ 8.82 (m, 0.7H), 8.78 (m, 0.3H), 8.62 (m, 0.3H), 8.54 (m, 0.7H), 8.37 (m, 1H), 7.93 (m, 0.3H), 7.87 (m, 0.7H), 7.80 (d, J=8.1, 2H), 7.43 (m, 2H), 7.32 (m, 4H), 7.12 (m, 1H), 6.68 (d, J=2.8, 0.3H), 6.62 (d, J=2.9, 0.7H), 6.02 (b, 0.7H), 5.71 (b, 0.3H), 5.13 (s, 2H), 4.61 (m, 0.3H), 4.27 (m, 0.7H), 4.04 (m, 0.7H), 3.78 (dd, J=5.2, 8.8, 0.3H), 3.48 (dd, J=3.3, 10.3, 0.7H), 3.27 (dd, J=3.3, 10.6, 0.3H).

IR (CDCl$_3$): 3500, 3100, 2980, 2920, 1695, 1595, 1470, 1450, 1370, 1255, 1175.

Mass Spectrum (DCI/NH$_3$): 416 [(M+1)$^+$, 100], 304 (60), 287 (25).

EXAMPLE 13.

Preparation of
1-[2-(3-pyridinyl)-thiazolid-4-oyl]-5,6-dimethoxyindole dihydrochloride 1-[2-(3-pyridinyl)-thiazolid-4-oyl]-5,6-dimethoxyindole was prepared using the method of Example 1, except 5,6-dimethoxyindole was used instead of 5-phenylmethoxyindole. The dihydrochloride salt was prepared as described in Example 2.

NMR (CDCl$_3$, 300 MHz): δ 3.38 (bs, 1H), 3.75-3.90 (c, 7H), 5.78 (bs, 1H), 6.48 (bs, 2H), 6.83 (bs, 1H), 7.17 (d, 1H, J=7.5 Hz), 7.25 (d, 1H, J=7.5 Hz), 7.58-7.85 (c, 2H), 7.91-8.11 (c, 1H), 8.81-9.02 (c, 1H), 9.43-9.57 (c, 1H).

EXAMPLE 14

Preparation of
1-[2-(3-pyridinyl)-thiazolid-4-oyl]-6-fluoroindole

1-[2-(3-pyridinyl)-thiazolid-4-oyl]-6-fluoroindole was prepared using the method of Example 1, except 6-fluoroindole was used instead of 5-phenylmethoxyindole.

NMR (CDCl$_3$, 300 MHz): δ 3.11 (bt, ½H, J=10.5 Hz), 3.26-3.37 (c, 1H), 3.49 (dd, 1H, J=10.5 Hz, 4.5 Hz), 3.61 (dd, ½H, J=10.5 Hz, 4.5 Hz), 4.58-4.71 (c, 1H), 5.71 (d, ½H, J=12 Hz), 6.01 (s, ½H), 6.67 (d, ½H, J=4.5 Hz), 6.73 (d, ½H, J=4.5 Hz), 7.04-7.13 (c, 1H), 7.39-7.49 (c, 1H), 7.42-7.55 (c, 2H), 7.85-7.91 (c, ½H), 7.93-7.99 (c, ½H), 8.20-8.30 (c, 1H), 8.53-8.57 (c, ½H), 8.62 (dd, ½H, J=3 Hz, 1.5 Hz), 8.82 (dd, 1H, J=10.5 Hz, 1.5 Hz).

Mass Spectrum (DCI/NH$_3$): 328(M+), 165, 107.

EXAMPLE 15

Preparation of
1-[2-(3-pyridinyl)-thiazolid-4-oyl]-6-chloroindole dihydrochloride 1-[2-(3-pyridinyl)-thiazolid-4-oyl]-6-chloroindole was prepared using the method of Example 1, except 6-chloroindole was used instead of 5-phenylmethoxyindole. The dihydrochloride salt was prepared as described in Example 2.

NMR (CDCl$_3$, 300 MHz): δ 3.6-3.2 (m, 2H), 3.8 (d, d, 1H, J=14 Hz, J=7 Hz), 5.4 (m, 1H), 5.6 (m, 1H), 6.18(m, 1H), 6.4 (m, 1H), 6.9 (m, 1H), 7.3 (m, 2H), 7.65 (m, 1H), 8.4-8.6 (m, 2H).

Mass Spectrum (DCI/NH$_3$): 344(M+), 343, 955

EXAMPLE 16

Preparation of
1-[2-(3-pyridinyl)-thiazolid-4-oyl]-6-bromoindole

1-[2-(3-pyridinyl)-thiazolid-4-oyl]-6-bromoindole was prepared using the method of Example 1 except 6-bromoindole was used instead of 5-phenylmethoxyindole.

NMR (CDCl$_3$, 300 MHz): δ 3.6-3.2 (m, 2H), 3.8 (dd, 1H, J=14 Hz, J=7 Hz), 5.4 (m, 1H), 5.6 (m,1H), 6.18 (m, 1H), 6.4 (m,1H), 6.9 (m, 1H), 7.3 (m. 2H), 7.65 (m, 1H), 8.6-8.4 (m, 2H).

EXAMPLE 17

Preparation of
1-(2-(3-pyridinyl)-thiazolid-4-oyl]-6-benzoylindole

1-[2-(3-pyridinyl)-thiazolid-4-oyl]-6-benzoylindole was prepared using the method of Example 1 except 6-benzoyloindole was used instead of 5-phenylmethoxyindole.

NMR (CDCl$_3$, 300 MHz): δ 3.35 (m), 3.48 (dd), 3.6 (d, d, J=10H, J=6 Hz, 2H), 4.65 (br m, 1H), 5.7 (d, 1H, J=10 Hz), 5.98 (br s, 1H), 6.8 (d,d 1H, J=6 Hz), 7.96-7.26 (m, 10H), 8.58 (dd, 1H, J=5 Hz, J=2 Hz), 8.67 (d, 1H, J=3 Hz), 8.83 (d, 1H, J=2 Hz), 8.93 (dd, 1H, J=1 Hz, J=9 Hz).

EXAMPLE 18

Preparation of
1-(2-(3-pyridinyl)thiazolid-4-oyl)-6-phenylmethoxyindole oxalate 1-(2-(3-pyridinyl)thiazolid-4-oyl)-6-phenylmethoxyindole was prepared using the method of Example 1, except 6-phenylmethoxyindole was used instead of 5-phenylmethoxyindole. The oxalate salt was prepared as described in Example 3.

NMR (CDCl$_3$, 300 MHz): δ 8.88 (d, 0.75 H, J=2.0), 8.81 (m, 0.25 H), 8.63 (m, 0.25H), 8.57 (dd, 0.75 H, J=0.5, 3.7), 8.21 (d, 0.75H, J=2.3), 8.18 (m, 0.25H), 7.95 (m, 1H), 7.35 (m, 7H), 7.04 (d, 1H, J=2.6), 7.01 (d, 1H, J=2.5), 6.68 (d, 0.25H), 6.63 (d, 0.75H, J=4.0), 6.04 (s, 0.75H), 5.71 (s, 0.25H), 5.16 (s, 1.5H), 5.14 (s, 0.5H), 4.66 (m, 0.75H), 3.64 (m, 0.25H), 3.48 (dd, 0.75H, J=6.9, 10.6), 3.29 (m, 0.25H), 3.27 (dd, 0.75H, J=7.3, 10.6).

IR (KBr): 3450 (br), 3160, 2900, 1695, 1605, 1430, 1380, 1280, 1235, 1205, 905.

Mass Spectrum (DCI/NH$_3$): 416 (M=1+, 65), 369, 339, 291, 287, 267 (100), 225.

EXAMPLE 19

Preparation of
1-[2-(3-pyridinyl)thiazolid-4-oyl]-7-aza-indole

1-[2-(3-pyridinyl)thiazolid-4-oyl]-7-aza-indole was prepared using the method of Example 1, except 7-aza-indole was used instead of 5-phenylmethoxyindole.

NMR (CDCl$_3$, 300 MHz): δ 3.19-3.27 (c, 1H), 3.72-3.82 (c, 1H), 5.98-6.10 (c, 1H), 6.22 (s, 1H), 6.93 (d, 1H, J=4.5 Hz), 7.21 (dd, 1H, J=21 Hz, 9 Hz), 7.35-7.42 (c, 1H), 8.02-8.11 (c, 2H), 8.15 (d, 1H, 7.5 Hz), 8.42 (d, 1H, J=4.5 Hz), 8.47 (t, 1H, J=4.5 Hz), 8.74 (d, 1H, J=4.5 Hz), 8.87 (d, 1H, J=4.5 Hz), 9.09 (d, 1H, J=9 Hz).

EXAMPLE 20

Preparation of 3-[2-(3-pyridinyl)-thiazolid-4-oyl]indole oxalate

Step 1.
2-(3-pyridinyl)-3-tert-butoxycarbonyl-4-thiazolidinecarboxyl chloride 2-(3-Pyridinyl)-3-tert-butoxycarbonyl-4-thiazolidinecarboxylic acid, (2 g, 0.0064 mol) prepared as described in Example 1 step 1, was added to a suspension of sodium hydride (0.15 g, 0.0064 mol) in benzene (40 mL) and methylene chloride (10 mL). The mixture was stirred until gas evolution ceased and then oxallyl chloride (0.6 mL, 0.0064 mol) was added giving a cloudy brown solution of the desired material which was carried on without isolation.

Step 2.
3-[2-(3-pyridinyl)-3-tert-butoxycarbonylthiazolid-4-oyl]indole

Indole (0.75 g, 0.0064 mol) in ether (20 mL) was added to ethylmagnesium chloride (3.2 ML, 2M in ether, 0.0064 mol). The mixture was allowed to stir for 20 minutes and was then added to a solution of 2-(3-pyridinyl)-3-tert-butoxycarbonyl-4-thiazolidinecarboxyl chloride prepared as described in step 1. The resulting mixture was stirred at room temperature for 1 hour at ambient temperature and then the reaction was quenched with saturated ammonium chloride. The solvent was removed from the organic phase and the residue was redissolved in methylene chloride. This was washed with sodium bicarbonate, dried over sodium sulfate and concentrated to give a brown solid. The desired compound was obtained (0.44 g) following purification with 30% ethyl acetate in hexanes.

Step 3. 3-[2-(3-pyridinyl)-thiazolid-4-oyl]indole

3-[2-(3-pyridinyl)-3-tert-butoxycarbonylthiazolid-4-oyl]indole (34 mg, 0.08 mmol) was dissolved in dioxane/hydrochloride and stirred at ambient temperature. After 2 h, the material was partitioned between ethyl acetate and sodium bicarbonate and then the organic phase was dried over magnesium sulfate and the solvent removed in vacuo to yield 3-[2-(3-pyridinyl)-thiazolid-4-oyl]indole (25 mg, 0.08 mmol).

NMR (CDCl$_3$, 300 MHz): $\delta$ 8.45 (m, 0.5 H), 8.80 (m, 0.5 H), 8.75 (b, 1H), 8.61 (m, 1H), 8.52 (m, 1H), 7.89 (m, 0.5H), 7.86 (m, 0.5 H), 7.58 (m, 0.5 H), 7.53 (d, J=4.1, 0.5 H), 7.44 (m, 0.5 H), 7.39 (m, 0.5 H), 7.32 (m, 2H), 6.77 (d, J=4.1, 0.5 H), 6.03 (b, 0.5H), 5.87 (b, 0.5H), 5.72 (b, 0.5H), 5.57 (b, 0.5H), 4.65 (m, 0.5H), 4.28 (m, 0.5H), 4.12 (m, 0.5H), 4.02 (m, 0.5H), 3.82 (m, 0.5H), 3.71 (m, 0.5H), 3.52 (m, 0.5H), 3.47 (m, 0.5H), 3.34 (m, 0.5H), 3.14 (m, 0.5 H).

IR (CDCl$_3$): 3500, 3300, 2960, 2940, 1710, 1705, 1450, 1395, 1350, 1205, 805.

Mass Spectrum (DCI/NH$_3$): 310 [(M+1)$^+$, 65], 267 (100), 225 (55), 207 (30), 165.

EXAMPLE 21

Preparation of 1,2-Dimethyl-3-[2-(3-pyridinyl)-thiazolid-4-oyl]indole oxalate

Aluminum chloride (2.9 g, 21.8 mmol) was added to a solution of 2-(3-pyridinyl)-3-tert-butoxycarbonyl-4-thiazolidinecarboxyl chloride, prepared as described in Example 1, step 1 (from 1.33 g of acid). After 5 minutes, 1,2-dimethyl indole (0.74 g, 0.0051 mol) was added in methylene chloride (5 mL). The mixture was stirred for 3 hours and then the reaction was quenched by the addition of saturated ammonium chloride solution (5 min). The mixture was partitioned between saturated sodium carbonate solution and methylene chloride. The organic phase was dried over MgSO$_4$ and the solvent evaporated. The resulting residue was chromatographed on silica gel, eluting with 1:1 ethyl acetate/hexanes to afford the desired material. The oxalate salt was prepared as described in Example 3.

NMR (CDCl$_3$, 300 MHz): $\delta$ 8.88 (m, 1H), 8.81 (d, 0.5H, J=2.2), 8.79 (d, 0.5H, J=2.2), 8.60 (dd, 0.5H, J=1.5, 4.8), 8.56 (dd, 0.5H, J=1.5, 4.8), 8.52 (m, 1H), 8.38 (m, 1H), 7.95 (m, 1H), 7.77 (m, 1H), 7.28 (m, 2H), 7.18 (d, 0.5H, J=1.5), 7.10 (d, 0.5H, J=3.6), 6.03 (s, 0.5H), 5.84 (s, 0.5H), 4.71 (m, 1H), 3.90 (s, 1.5H), 3.86 (s, 1.5H), 3.53 (m, 0.5H), 3.41 (m, 0.5H), 3.22 (dd, 0.5H, J=1.1, 10.7), 3.14 (dd, 0.5H, J=2.2, 10.7)

Mass Spectrum (DCI/NH$_3$): 324 [(M+1)$^+$, 40], 296 (85), 190 (70), 107 (100).

EXAMPLE 22

Preparation of 1-Methyl-3-[2-(3-pyridinyl)-thiazolid-4-oyl]indole dihydrochloride The desired material was prepared using the method of Example 21, except using 1-methylindole instead of 1,2-dimethylindole. The dihydrocloride salt was prepared as described in Example 2.

NMR (CDCl$_3$, 300 MHz): $\delta$ 8.88 (m, 1H), 8.81 (d, 0.5H, J=2.2), 8.79 (d, 0.5H, J=2.2), 8.60 (dd, 0.5H, J=1.5, 4.8), 8.56 (dd, 0.5H, J=1.5, 4.8), 8.52 (m, 1H), 8.38 (m, 1H), 7.95 (m, 1H), 7.77 (m, 1H), 7.28 (m, 2H), 7.18 (d, 0.5H, J=1.5), 7.10 (d, 0.5H, J=3.6), 6.03 (s, 0.5H), 5.84 (s, 0.5H), 4.71 (m, 1H), 3.90 (s, 1.5H), 3.86 (s, 1.5H), 3.53 (m, 0.5H), 3.41 (m, 0.5H), 3.22 (dd, 0.5H, J=1.1, 10.7), 3.14 (dd, 0.5H, J=2.2, 10.7)

Mass Spectrum (DCI/NH$_3$): 324 [(M+1)$^+$, 40], 296 (85), 190 (70), 107 (100).

EXAMPLE 23

Preparation of 3-(2-(3-pyridinyl)thiazolid-4-oyl)-5-phenylmethoxyindole oxalate

Step 1.
3-[2-(3-pyridinyl)-3-tert-Butoxycarbonyl-thiazolid-4-oylmethyl]-5-phenylmethoxyindole.

Ethyl magnesium chloride (4.0 mL, 2M, 0.0008 mol) was added to a solution of 5-phenylmethoxyindole (1.91 g, 0.0086 mol) in ether (90 mL) and the mixture was stirred for 30 minutes. 2-(3-pyridinyl)-3-tert-butoxycarbonyl-4-thiazolidinecarbonyl chloride prepared as described in 20, step 1 (1.29 g, 0.0039 mol) in (110 mL) was then added and the resulting suspension was stirred at ambient temperature for 2 h. The solvent was removed in vacuo and the resulting residue partitioned between saturated ammonium chloride solution and ether. The organic phase was subsequently washed with saturated sodium chloride and dried over magnesium sulfate. The solvent was removed and the residue chromatographed on silica gel eluting first with 2:1 ethyl acetate: hexane and then with ethyl acetate. The desired compound (0.133 g) was isolated.

Step 2.
3-[2-(3-pyridinyl)-thiazo-4-oyl]-5-phenylmethoxyindole

3-[2-(3-pyridinyl)-3-tert-Butoxycarbonyl-thiazolid-4-oylmethyl]-5-phenylmethoxyindole (0.120 g, 0.23 mmol) was deprotected in hydrochloric acid/dioxane to yield 3-[2-(3-pyridinyl)-thiazo-4-oyl]-5-phenylmethoxyindole (0.054 g). The oxalate salt was prepared as described in Example 3.

NMR (CDCl$_3$, 300 MHz): δ 8.84 (bs, 0.5H), 8.79 (d, 0.5H, J=2.2), 8.61 (dd, 0.5H, J=1.5, 4.8), 8.53 (dd, 0.5H, 0.7, 4.8), 8.02 (m, 1H), 7.96 (d, 0.5H, J=2.9), 7.89 (d, 0.5H, J=3.3), 7.51 (bs, 0.5H), 7.48 (bs, 0.5H), 7.42 (d, 0.5H, J=1.4), 7.39 (d, 0.5H, J=1.5), 7.33 (m, 5H), 7.05 (m, 2H), 6.03 (s, 0.5H), 5.72 (bs, 0.5H), 5.16 (s, 2H), 4.69 (m, 0.5H), 4.58 (m, 0.5H), 3.52 (dd, 0.5H, J=7.3, 10.6), 3.38 (dd, 0.5H, J=7.0, 10.3), 3.18 (m, 1H).

IR (CDCl$_3$): 3440 (br), 3180, 3050, 2930, 2900, 1620, 1600, 1515, 1470, 1450, 1420, 1375, 1260, 1190, 800. 730, 705.

Mass Spectrum (DCI/NH$_3$): 416 [(M+1)$^+$, 90], 313 (85), 250 (100).

EXAMPLE 24

Preparation of 3-(2-(3-pyridinyl)thiazolid-4-oyl)-4-phenylmethoxyindole oxalate 3-(2-(3-Pyridinyl)thiazolid-4-oyl)-4-phenylmethoxyindole was prepared as described in Example 23, except 4-phenylmethoxyindole was used instead of 5-phenylmethoxyindole. The oxalate salt was prepared as described in Example 3.

NMR (CDCl$_3$, 300 MHz): δ 8.86 (m, 0.5H), 8.78 (m, 0.5H), 8.62 (m, 0.5H), 8.56 (m, 0.5H), 8.00 (m, 0.5H), 7.97 (m, 0.5H), 7.92 (m, 1H), 7.5–7.3 (m, 6H), 7.24 (m, 1H), 7.06 (m, 1H), 6.61 (dd, J=2.9, 6.8, 0.5H), 6.58 (dd, 1.8, 6.5, 0.5H), 6.08 (bs, 0.5H), 5.86 (bs, 0.5H), 5.28 (s, 1H), 5.22 (s, 1H), 4.78 (m, 0.5H), 4.60 (m, 0.5H), 3.62 (m, 0.5H), 3.53 (m, 0.5H), 3.24 (m, 1H).

Mass Spectrum (DCI/NH$_3$): 416 [(M+1)$^+$, 86], 326 (95), 292 (60), 107 (100).

Exact Mass: Theoretical: 416.143; Experimental: 416.142.

EXAMPLE 25

Preparation of 3-(2-(3-pyridinyl)thiazolid-4-oyl)-7-methylindole oxalate

Step 1. 1-[2-(3-pyridinyl)thiazolid-4-oyl]-imidazole

Carbonyl diimidazole (0.724 g, 0.00447 mol) was added to a solution of 2-(3-pyridinyl)-3-tert-butoxycarbonyl-4-thiazolidinecarboxylic acid, prepared as described in Example 1, step 2 (1.32 g, 0.00426 mol) in methylene chloride (40 mL). After stirring the reaction mixture for 3 hours the solution was extracted with saturated sodium chloride and dried over magnesium sulfate. The solvent was removed in vacuo to afford 1.03 g of the desired product as a beige solid.

Step 2.
3-(2-(3-pyridinyl)thiazolid-4-oyl)-7-methylindole oxalate 3-(2-(3-pyridinyl)thiazolid-4-oyl)-7-methylindole oxalate was prepared using the method of Example 23, except 7-methylindole was used instead of 5-phenylmethoxyindole and 1-[2-(3-pyridinyl)thiazolid-4-oyl]-imidazole was used instead of 2-(3-pyridinyl)-3-tert-butoxycarbonyl-4-thiazolidinecarbonyl chloride. The salt was prepared as described in Example 3.

NMR (CDCl$_3$, 300 MHz): δ 4.72 (dd, 0.6H, J=5.2, 7.4), 4.61 (dd, 0.4H, J=5.2, 8.8), 3.71 (s, 3H), 3.63 (dd, 0.4H, J=5,2, 10.3), 3.52 (dd, 0.6H, J=5.2, 10.2), 3.34 (0.4H, J=8.8, 10.3), 3.17 (dd, 0.6H, J=7.4, 10.2).

Exact Mass: Theoretical: 324.117; Experimental: 324.117.

EXAMPLE 26

Preparation of 1-[2-(3-pyridinyl)-dithiolan-4-oly]indole oxalate

Step 1. Methyl 2,3-dimercaptopropenonate

To a flame dried 1 liter 3-neck flask 30 g (1.25 mol, 5.8 eq) of sodium spheres (rinsed with hexanes) were added. The flask was equipped with an addition funnel and a reflux condenser. Anhydrous methanol (400 mL) was added to the sodium metal via the addition funnel in a dropwise fashion Once all the sodium was in solution (approximately 45 minutes), the reaction was cooled to 0° C. and saturated with gaseous H$_2$S for 1 hr. During the course of the addition, excess H$_2$S was neutralized by bubbling the bleed line through a trap containing a 10% solution of aqueous sodium hydroxide. A solution of 50.0 g (0.22 mol, 1 eq.) 2,3-dibromopropionic acid dissolved in 100 ml of methanol was added to the reaction mixture via the addition funnel at a rapid drip rate. The solution was allowed to warm to room temperature and was stirred an additional 18 hr.

The reaction was then acidified to pH of 2 by initial dropwise addition of 100 mL of saturated methanolic HCl (H$_2$S evolution observed) followed by bubbling gaseous HCl into the reaction mixture until the desired pH was obtained. At this point, a thick white precipitate was present. The solution was stirred for an additional 4 hours and then concentrated on a rotoevaporator to remove the methanol. The resulting pasty residue was partitioned between 300 mL of water and 300 mL of ethyl ether. The aqueous phase was extracted with ethyl ether (2×) and the combined organic extracts washed once with brine and dried over magnesium sulfate. The drying agent was filtered off and the filtrate concentrated in vacuo to yield methyl 2,3-dimercaptopropenonate (28.5 g, 86.5%) as a light yellow oil.

Step 2. Methyl 2-(3-pyridinyl)-4-dithiolanecarboxylate

To a 3-neck round bottomed flask equipped with a Dean Stark trap and a constant rate addition funnel was added 7.05 g (65.7 mmol, 1.0 eq.) of 3-pyridinealdehyde and 15.0 g (78.9 mmol, 1.2 eq.) p-toluenesulfonic acid in 350 mL of toluene, 25 ml of 2-butanol, and 15 ml 1-butanol. The solution was heated to reflux, whereupon 10.0 g (65.7 mmol, 1 eq.) of methyl 2,3-dimercaptopropenonate as prepared in step 1, above, in 30 mL toluene was added dropwise over ninety minutes to the refluxing reaction mixture via the addition funnel. The reaction was allowed to reflux overnight and the following day cooled to room temperature and concentrated in vacuo. The residue was partitioned between saturated aqueous sodium bicarbonate and ethyl acetate (requires agitation for >30 min). The aqueous phase was extracted one more time with ethyl acetate. The combined organic extracts were then washed successively with saturated aqueous sodium bisulfite (×2), 1M aqueous sodium hydroxide (×2), and saturated aqueous brine (×1), dried over sodium sulfate, filtered and concentrated in vacuo to afford 18.57 g (117% crude yield) of a brown oil. TLC showed predominantly desired material along with some 3-pyridine carboxaldehyde and a much less polar impurity. the oil was purified by flash chromatography ($SiO_2$, 80:20 hexanes:ethyl acetate). Methyl 2-(3-pyridinyl)-4-dithiolanecarboxylate was isolated in fractions 85–195 as 8.03 g (50.6% yield) of an orange oil.

NMR ($CDCl_3$, 300 MHz) δ 3.45 (dd, 0.5H), 3.6 (dd, 0.5H), 3.65 (dd, 0.5H), 3.7 (dd, 0.5H), 3.8 (s, 1.5H), 3.82 (s, 1.5H), 4.5 (t, 0.5H), 4.65 (t, 0.5H), 5.65 (s, 0.5H), 5.75 (s, 0.5H), 7.3 (dd, 1H), 7.95 (ddt, 1H), 8.5 (td, 1H), 8.7 (dd, 1H).

Step 3. 2-(3-pyridinyl)-4-dithiolanecarboxylic acid

Dithiolane ester (2 g, 8.3 mmol, 1 eq.), prepared as in step 2 above, was dissolved in a 3:1 (v/v) solution of tetrahydrafuran and $H_2O$ and 432 mg of lithium hydroxide hydrate (10 mmol, 1.2 eq.) added in one portion. The reaction immediately assumed an orange color. After 10 min, thin layer chromatography showed complete consumption of starting ester. The reaction was concentrated in vacuo to remove tetrahydrofuran and the resulting aqueous solution extracted with ether (2×) to remove any impurities. The aqueous phase was acidified to a pH of 4 with 1N aqueous HCl and concentrated in vacuo. The resulting oily residue was then ultrasonicated with tetrahydrofuran and ethanol and vacuum filtered. The filtrate was concentrated in vacuo and chased two times with toluene to afford 1.6 g (85% yield) of 2-(3-pyridinyl)-4-dithiolanecarboxylic acid as a yellow solid.

Step 4. 1-[2-(3-pyridinyl)dithiolan-4-oyl]-imidazole

The desired compound was prepared according to the method of Example 25, step 1, except using 2-(3-pyridinyl)-4-dithiolanecarboxylic acid instead of 2-(3-pyridinyl)-3-tert-butoxycarbonyl-4-thiazolidinecarboxylic acid.

Step 5. 1-[2-(3-pyridinyl)-dithiolan-4-oyl]indole

Indole (0.25 g, 0.0021 mol) was dissolved in ether (20 mL) and the mixture heated until it began to reflux. Ethyl magnesium bromide (1.0 mL, 2.0 mmol in ether, 0.002 mol) was added, followed 15 min later by 1-[2-(3-pyridinyl)dithiolan-4-oyl]-imidazole, prepared as described in step 4 above, (0.267 g, 0.00096 mol) in methylene chloride (15 mL). After heating at reflux temperature for 5.5 hr the mixture was partitioned between saturated ammonium chloride (50 mL) and methylene chloride. The organic phase was dried over $MgSO_4$ and the solvent evaporated. After purification by column chromatography the desired compound was obtained. The oxalte salt was prepared as described in Example 3.

NMR ($CDCl_3$, 300 MHz): δ 8.84 (dd, 0.5H, J=2.2, 4.5), 8.76 (dd, 0.5H, J=2.8, 4.5), 8.51 (m, 1H), 8.19 (t, 0.5H, =1.6), 8.16 (t, 0.5H, J=2.2), 7.29 (m, 1H), 7.62 (bd, 0.5H, J=6.0), 7.58 (m, 0.5H), 7.27 (m, 3H), 7.05 (m, 1H), 6.68 (dd, 0.5H, J=1.0, 2.9), 6.57 (dd, 0.5H, J=1.2, 3.0), 5.82 (s, 0.5H), 5.77 (s, 0.5H), 4.64 (dd, 0.5H, J=5.5, 6.1), 4.49 (dd, 0.5H, J=5.8, 6.1), 4.08 (dd, 0.5H, J=5.8, 11.2), 4.02 (dd, 0.5H, J=2.5, 8.5), 3.56 (dd, 0.5H, J=6.0, 9.1), 3.42 (dd, 0.5H, J=3.0, 10.5)

Mass Spectrum ($DCI/NH_3$): 344 [(M+$NH_4$)+, 5],327 [(M+1)+, 50], 242 (30), 124 (55), 108 (100).

EXAMPLE 27

Preparation of 1-Ethyl-3-[2-(3-pyridinyl)-thiazolid-4-oyl]indole oxalate

Step 1. 1-Ethyl-3-[2-(3-pyridinyl)-3-tert-butoxycarbonyl-thiazolid-4-oyl]indole

Potassium hexamethyldisilazide (1.2 mL, 0.5 M in toluene, 0.0006 mol) was added to a solution of 3-[2-(3-pyridinyl)-3-tert-butoxycarbonylthiazolid-4-oyl]indole prepared as described in Example 25 in tetrahydrofuran (10 mL) at −78° C. The mixture was stirred for 20 minutes and then ethyl iodide (0.25 mL, 0.00031 mol) was added. After an additional 50 min of stirring the reaction mixture was allowed to warm to room temperature. Sixty min. later the solvent was removed and the residue partitioned between saturated $NH_4Cl$ solution and ether. The organic phase was dried over $MgSO_4$. The solvent was removed in vacuo to give the desired material which was carried on without further purification.

Step 2. 1-Ethyl-3-[2-(3-pyridinyl)-thiazolid-4-oyl]indole oxalate

1-Ethyl-3-[2-(3-pyridinyl)-3-tert-butoxycarbonyl-thiazolid-4-oyl]indole was deprotected with HCl in dioxane to give 1-Ethyl-3-[2-(3-pyridinyl)-thiazolid-4-oyl]indole oxalate. The oxalate salt was prepared using the procedure described in Example 3.

NMR ($CDCl_3$, 300 MHz): δ 8.88 (m, 0.4H), 8.79 (d, 0.6H, J=1.2), 8.60 (dd, 0.6H, J=1.2, 4.8), 8.55 (m, 0.4H), 8.39 (m, 1H), 7.99 (m, 0.6H), 7.95 (m, 0.4H), 7.93 (s, 0.6H), 7.85 (s, 0.4H), 7.41 (m, 1H), 7.35 (m, 4H), 6.06 (s, 0.4H), 5.74 (s, 0.6H), 4.70 (dd, 0.6H, J=7.0, 9.8), 4.58 (dd, 0.4H, J=8.4, 9.6), 4.28 (q, 0.6H, J=7.3), 4.24 (q, 0.4H, J=7.3), 3.54 (dd, 0.6H, J=6.9, 10.3), 3.42 (dd, 0.4H, J=9.6, 16.6), 3.21 (dd, 0.6H, J=9.8, 10.3), 3.12 (dd, 0.4H, J=8.4, 10.3), 1.59 (t, 0.6H, J=7.0), 1.55 (t, 0.4H, J=7.3)

IR ($CDCl_3$): 3680, 2960, 2920, 1705, 1635, 1520, 1390, 1130.

Mass Spectrum ($DCI/NH_3$): 338 [(M+1)+, 100], 235 (20), 216 (40), 146 (45), 107 (100)

Exact Mass: Theoretical: 338.132; Experimental: 338.132.

EXAMPLE 28

Preparation of 1-tert-Butoxycarbonyl-3-[2-(3-pyridinyl)-thiazolid-4-oyl]indole oxalate Ditert-butyl dicarbonate (0.15 g, 0.00069 mol) was added to a solution of 3-[2-(3-pyridinyl)-3-thiazolid-4-oyl]indole prepared as described in Example 20 (0.2 g, 0.00065 mol) and dimethylaminopyridine (9 mg) in acetonitrile (6.5 mL) and the mixture was stirred overnight. The mixture was then partitioned between saturated $NH_4Cl$ and ethyl acetate. The organic phase was washed with saturated $NaHCO_3$ solution and dried over magnesium sulfate. The oxalate salt was prepared as described in Example 3. NMR (CDCl$_3$, 300 MHz): δ 8.52 (dd, 0.5H, J=1.5, 4.8), 8.45 (dd, 0.5H, J=1.5, 4.8), 8.34 (s, 0.5H), 8.32 (sa, 0.5H), 8.18 (m, 0.5H), 8.15 (m, 0.5H), 8.11 (m, 0.5H), 8.07 (m, 0.5H), 7.46–7.38 (m, 3H), 7.37 (d, 0.5H, J=1.5), 7.34 (d, 0.5H, J=1.0), 5.90 (bs, 0.5H), 5.75 (bs, 0.5H), 4.93 (m, 1H), 3.60 (dd, 0.5H, J=7.3, 10.3), 3.49 (dd, 0.5H, J=7.4, 10.3), 3.24 (m, 1H), 1.73 (s, 4.5H), 1.70 (s, 4.5H)

IR (CDCl$_3$): 2980, 2920, 1735, 1660, 1445, 1370, 1235, 1045.

Mass Spectrum (DCI/NH$_3$): 410 [(M+1)$^+$, 100], 376 (10), 310 (10).

EXAMPLE 29

Preparation of cis 1-tert-Butoxycarbonyl-3-[2-(3-pyridinyl)-dithiolan-4-oyl]indole hydrochloride Step 1.
N-Methoxy-N-methyl-2-(3-pyridinyl)-4-dithiolanecarboxamide.

N-methoxy-N-methyl amine (1.82 g, 0.018 mol) was added to a solution of 2-(3-pyridinyl)-4-dithiolanecarboxylic acid, prepared as described in Example 25 (2.97 g, 13.1 mol), dimethylaminopyridine (94 mg, 0.0008 mol), and N-methylmorpholine (4.5 mL, 0.0041 mol) in Dimethylformamide (15 mL) and methylene chloride (150 mL). Bis(2-oxo-3-oxazolidinyl)phosphinic chloride (5.0 g, 0.0197 mol) was then added and the clear solution stirred overnight. The reaction mixture was partitioned between saturated NaHCO$_3$ (200 mL) and methylene chloride (400 mL). The organic phase was washed with saturated NaCl and dried over MgSO$_4$. The solvent was removed in vacuo and the residue chromatographed on silica gel eluting with 2:1 ethylacetate/hexanes to obtain the desired compound (2.21 g, 62%).

Step 2.
1-Tert-butoxycarbonyl-3-[2-(3-pyridinyl)-dithiolan-4-oyl]indole oxalate tert-Butyl lithium (19.4 mL, 1.7M, 0.033 mol) was added to a solution of 1-tert-butoxycarbonyl-3-bromo indole (4.96 g, 0.016 mol) in ether (170 mL) at −78° C. Twelve min later N-methoxy-N-methyl-2-(3-pyridinyl)-4-dithiolanecarboxamide (1.45 g, 0.0054 mol) in ether (20 mL) was added. The suspension was stirred at −78° C. for 1 h. and then allowed to warm to room temperature. The mixture was partitioned between ether (350 mL) and saturated ammonium chloride solution (350 mL). The organic phase was reextracted with 200 mL of ethyl acetate and the combined organic phases were dried over MgSO$_4$. The solvent was removed in vacuo and the residue chromatographed on silica gel to give the desired product as a tan solid (1.14 g, 50%). The oxalate salt was prepared as described in Example 3.

NMR (CDCl$_3$, 300 MHz): δ 8.67 (d, 1H, J=1.5), 8.50 (dd, 1H, J=1.5, 4.8), 8.41 (m, 1H), 8.31 (s, 1H), 8.12 (m, 1H), 8.03 (m, 1H), 7.41 (m, 2H), 7.32 (d, 1H, J=4.8), 5.75 (s, 1H), 5.15 (~t, 1H, J=6.0), 4.03 (dd, 1H, J=6.2, 12.1), 3.49 (dd, J=5.8, 12.2), 1.72 (s, 9H)

EXAMPLE 30

Preparation of trans 1-Tert-butoxycarbonyl-3-[2-(3-pyridinyl)-dithiolan-4-oyl]indole oxalate The desired compound was obtained along with the cis isomer from the sequence described in Example 29. It was isolated from mixed fractions obtained during the chromatographic purification described in Example 19, step 2. The desired compound was purified by high pressure liquid chromatography on silica gel eluting with 2:1 ethyl acetate/hexanes. The oxalate salt was prepared as described in Example 3.

NMR (CDCl$_3$, 300 MHz): δ 8.78 (d, 1H, J=1.6), 8.55 (dd, 1H, J=1.6, 4.9), 8.39 (m, 1H), 8.30 (s, 1H), 8.12 (m, 1H), 7.98 (m, 1H), 7.41 (m, 2H), 7.29 (d, 1H, J=5.1), 5.77 (s, 1H), 5.32 (~t, 1H, J=5.9), 3.96 (dd, 1H, J=5.9, 12.0), 3.60 (dd, 1H, J=5.9, 11.8), 1.71 (s, 9H).

EXAMPLE 31

Preparation of 3-[2-(3-pyridinyl)-dithiolan-4-oyl]indole oxalate

Sodium methoxide in methanol (0.75 mL, 2.0M, 1.5 mmol) was added to a solution of 1-tert-butoxycarbonyl-3-[2-(3-pyridinyl)-dithiolan-4-oyl]indole oxalate (0.21 g, 0.49 mmol) in tetrahydrofuran. After ten min. the reaction mixture was partitioned between saturated sodium chloride (20 mL) and ethyl acetate (60 mL). The organic phase was dried over magnesium sulfate and the solvent evaporated. The residue was chromatographed on silica gel, eluting with 2:1 ethyl acetate/hexanes to give the desired compound. The oxalate salt was prepared as descibed in Example 3.

NMR (CDCl$_3$, 300 MHz): δ 8.69 (d, 0.5H, J=1.9), 8.66 (d, 0.5H, J=1.8), 8.43 (dd, 0.5H, J=1.5, 9.6), 8.38 (dd, 0.5H, J=1.5, 4.8), 8.28 (m, 1H), 8.20 (s, 0.5H), 8.18 (s, 0.5H), 8.08 (t, 0.5H, J=2.1), 8.05 (m, 0.5H), 7.45 (m, 1H), 7.34 (m, 2H), 7.24 (m, 2H), 5.82 (s, 0.5H), 5.81 (s, 0.5H), 5.54 (t, 0.5H, J=5.9), 5.36 (dd, 0.5H, J=5.9, 7.0), 3.87 (dd, 0.5H, J=7.3, 12.2), 3.83 (dd, 0.5H, J=5.9, 12.1), 3.64 (dd, 0.5H, J=5.8, 11.8), 3.38 (dd, 0.5H, J=5.6, 12.2).

Mass Spectrum (DCI/NH$_3$): 327 [(M+1)$^+$, 5], 124 (100).

EXAMPLE 32

Preparation of 1-Phenylsulfonyl 3-[2-(3-pyridinyl)-dithiolan-4-oyl]indole oxalate The desired compound was prepared according to the procedure of Example 29, except using 3-bromo-1-phenylsulfonyl indole instead of 3-bromo-1-tert-butoxycarbonyl indole.

NMR (CDCl$_3$, 300 MHz): δ 8.76 (d, 0.6H, J=2.2), 8.68 (d, 0.4H, J=2.3), 8.57 (dd, 0.6H, J=1.5, 4.8), 8.51 (dd, 0.4H, J=1.8, 5.1), 8.36 (m, 1H), 8.31 (s, 0.4H), 8.29 (s, 0.6H), 8.02 (m, 1H), 7.96 (m, 2H), 7.60 (m, 2H), 7.50 (m, 2H), 7.40 (m, 3H), 7.36 (m, 1H), 5.78 (s, 0.4H), 5.72 (s, 0.6H), 5.32 (t, 0.6H, J=5.9), 5.15 (t, 0.4H, J=5.9), 4.01 (dd, 0.4H, J=6.2, 12.5), 3.95 (dd, 0.6H, J=5.5, 11.8), 3.65 (dd, 0.6H, J=6.3, 12.2), 3.49 (dd, 0.4H, J=5.9, 12.5).

IR (CDCl$_3$): 3120, 3050, 2980, 2940, 1670, 1535, 1445, 1380, 1190, 1180, 1140.

Mass Spectrum (DCI/NH$_3$): 467 [(M+1)$^+$, 100], 312 (50), 172 (75).

EXAMPLE 33

Preparation of
3-[2-(3-pyridinyl)-thiazolid-4-ylmethyl]indole
dihydrochloride

Step 1.
1-Indol-3-yl-2-tert-butoxycarbonylamino-3-hydroxy
propane

Borane-tetrahydrofuran (165 mL, 1M in THF, 0.165 mol) was added to a solution of BOC-D-tryptophan (10 g, 0.033 mol) in THF (250 mL) at 0° C. The reaction mixture was stirred overnight and then quenched with methanol (50 mL). The mixture was poured into water (200 mL) and the organic layer separated, dried over sodium sulfate and the solvent removed in vacuo. The resulting residue was purified by chromatography on silica gel eluting with 1:1 ethyl acetate/hexanes to yield 5.13 g (54%) of the desired product.

Step 2.
1-Indol-3-yl-2-tert-butoxycarbonylamino-3-thioacetoxy
propane

Di-isopropyl azodicarboxylate (3.48 mL, 0.017 mol) was added to a solution of triphenyl phosphine (4.63 g, 0.017 mol) in THF (75 mL). The mixture was stirred at 0° C. for 30 min and then a solution of 1-indol-3-yl-2-tert-butoxycarbonylamino-3-hydroxy propane, prepared as described above in step 1 (5.1 g, (0.017 mol) and thioacetic acid (1.26 mL, 0.176 mmol) in THF was added. The reaction mixture was stirred overnight and then the solvent was remove in vacuo. The residue was purified by chromatography on silica gel eluting with 2:1 ethyl acetate/hexanes to yield 4.97 g of the desired product.

Step 3. 1-Indol-3-yl-2-amino-3-mercaptopropane

A mixture of 1-indol-3-yl-2-tert-butoxycarbonylamino-3-thioacetoxy propane (3.0 g, 0.0086 mol) in methanol (20 mL) was heated at 60° C. for 30 min. The mixture was poured into saturated citric acid (200 mL) and then extracted with methylene chloride. The organic phase was dried over sodium sulfate and the solvent evaporated. The residue was dissolved in acetic acid (10 mL) and HCl in acetic acid (10 mL) was added. The mixture was allowed to stand at room temperature for 45 min and the desired material precipitated with the addition of 200 mL of ether. The precipitate was collected by filtration and partitioned between saturated sodium bicarbonate solution and methylene chloride. The organic phase was separated, dried over sodium sulfate and the solvent evaporated to give 650 mg of the desired compound as a gray oil. This was carried on to the next step without further purification.

Step 4. 3-[2-(3-pyridinyl)-thiazolid-4-ylmethyl]indole

3-Pyridine aldehyde (0.30 mL, 0.0032 mol) was added to a solution of 1-indol-3-yl-2-amino-3-mercaptopropane (650 mg) in ethanol (10 mL) and the mixture stirred overnight. The solvent was removed in vacuo and the residue chromatographed on silica gel eluting with 2:1 ethyl acetate/hexanes to the desired compound.

Step 5. 3-[2-(3-pyridinyl)-thiazolid-4-ylmethyl]indole dihydrochloride.

Saturated HCl in ether (10 mL) was added to a solution of 3-[2-(3-pyridinyl)dithiolan-4-ylmethyl]indole in ethylacetate (5 mL). The resulting solid was collected by filtration and dried in vacuo to provide the desired compound (187 mg) as a crystalline solid.

NMR (CDCl$_3$, 300 MHz): δ 2.87 (c, 1H), 3.20 (c, 3H), 3.73 (m, 1H), 5.60 (s, 0.66H), 5.77 (s, 0.33H), 7.10–7.30 (m, 3H), 7.38–7.52 (m, 1H), 7.62–7.90 (m, 2H), 8.19–8.21 (m, 1H), 8.50–8.80 (m, 2H), 8.82–9.08 (m, 1H), 10.13 (s, 1H).

Mass Spectrum (DCI/NH$_3$): 296 (M+H)$^+$.

EXAMPLE 34

Preparation of
6-Phenylemthoxy-3-[2-(3-pyridinyl)-thiazolid-4-oyl]indole

The desired material was prepared using the method of Example 20, except using 6-phenylmethoxy indole instead of indole and methyl magnesium bromide instead of ethyl magnesium bromide.

Melting Point: 193°–195° C.

NMR (CDCl$_3$, 300 MHz): δ 8.85 (d, 0.4H, J=1.2), 8.79 (d, 0.6H, J=1.4), 8.60 (m, 0.6H), 8.52 (m. 0.4H), 8.28 (s, 0.6H), 8.26 (s, 0.4H), 7.97 (m, 0.6H), 7.91 (d, 0.6H, J=7.8), 7.88 (m, 0.4H), 7.83 (d, 0.4H, J=7.6), 7.40 (m, 6H), 7.27 (m, 1H), 7.08 (m, 1H), 6.98 (d, 0.6H, J=2.2), 6.95 (d, 0.4H, J=2.3), 6.03 (s, 0.4H), 5.72 (s, 0.6H), 5.14 (s, 2H), 4.70 (dd, 0.6H, J=7.0, 7.7), 4.57 (dd, 0.4H, J=7.0, 7.2), 3.52 (dd, 0.6H, J=7.0, 10.3), 3.38 (dd, 0.4H, J=7.0, 9.2), 3.18 (m, 1H).

IR (KBr): 3420, 3250, 2920, 1630, 1525, 1420, 1175.

Mass Spectrum (DCI/NH$_3$): 416 [(M+1)$^+$, 35], 185 (100).

Elemental Analysis: Theoretical: C: 69.38, H: 5.09, N: 10.11; Found: C: 69.23, H: 5.15, N:9.92.

EXAMPLE 35

Preparation of
1-tert-Butoxycarbonyl-6-phenylmethoxy-3-[2-(3-pyridinyl)-thiazolid-4-oyl]indole oxalate The desired compound was prepared using the procedure of Example 28, except using 6-phenylmethoxy-3-[2-(3-pyridinyl)-thiazolid-4-oyl]indole prepared as described in Example 33, instead of 3-[2-(3-pyridinyl)-thiazolid-4-oyl]indole. The oxalate salt was prepared as described in Example 3.

NMR (CDCl$_3$, 300 MHz): δ 8.83 (d, 0.2H), 8.79 (d, 0.8H, J=1.9), 8.62 (dd, 0.8H, J=1.8, 5.1), 8.55 (dd, 0.2H), 8.26 (s, 0.8H), 8.23 (s, 0.2H), 7.97 (ddd, 0.8H, J=1.9, 2.3, 7.8), 7.88 (m, 0.2H), 7.80 (d, 1H, J=2.3), 7.41 (m, 7H), 7.10 (dd, 1H, J=2.2, 8.8), 6.03 (s, 0.2H), 5.73 (s, 0.8H), 5.15 (s, 2H), 4.70 (dd, 0.8H, J=7.3, 9.1), 4.64 (m, 0.2H), 3.56 (dd, 0.8H, J=7.3, 10.3), 3.44 (dd, 0.2H), 3.17 (dd, 0.8H, J=9.2, 10.3), 3.15 (dd, 0.2H), 1.71 (s, 7.2H), 1.68 (s, 1.8H).

IR (KBr): 3440 (br), 2970, 2920, 1740, 1660, 1615, 1490, 1370, 1275, 1210, 1140.

Mass Spectrum (FAB): 561 [(M+1)$^+$, 7], 307 (15), 154 (100).

EXAMPLE 36

Preparation of
1-Phenylsulfonyl-3-[2-(3-pyridinyl)-thiazolid-4-oyl]indole

Step 1.
1-Phenysulfonyl-3-[2-(3-pyridinyl)-3-tert-butoxycarbonylthiazolid-4-oyl]indole Powdered KOH (0.17 g, 0.0031 mol) was added to a solution of 3-[2-(3-pyridinyl)-3-tert-butoxycarbonyl-thiazolid-4-oyl]indole, prepared as described in Example 20, steps 1, 2 (0.25 g, 0.00061 mol) in dimethoxyethane (9 mL) at 0° C. Ten minutes later, benzene sulfonyl chloride (0.00067 mol) was added and the mixture stirred an additional 30 min. at room temperature. Benzene was added to the mixture and the insoluble materials were removed by filtration. The filtrate was washed with saturated sodium chloride solution and dried over sodium sulfate. The solvent was evaporated to afford a crystalline residue (340 mg).

Step 2.
1-Phenylsulfonyl-3-[2-(3-pyridinyl)-thiazolid-4-oyl]indole

The material prepared in step 1 above was deprotected using the method of Example 1, step 5, except using trifluoroacetic acid in methylene chloride instead of HCl in dioxane to afford the desired compound.

NMR (CDCl$_3$, 300 MHz): δ 1.18-1.36 (t, 3H, J=7.4 Hz), 3.1-3.25 (m, 2H), 3.45-3.58 (m, 2H), 4.58 (t, 0.5, J=7.4 Hz), 4.69-4.75 (m, 0.5H), 5.74 (s, 0.5H), 6.5 (s, 0.5H), 7.35-7.45 (m, 2H), 7.46-7.51 (m, 3H), 7.6-7.68 (m, 1H), 8.02-8.06 (c, 0.5H), 8.23 (c, 0.5H), 8.41-8.46 (m, 1H), 8.59-8.65 (m, 1H), 8.82 (d, 0.5H, J=1.8 Hz), 8.97 (bs, 0.5H)

EXAMPLE 37

Preparation of
1-Methylsulfonyl-3-[2-(3-pyridinyl)-thiazolid-4-oyl]indole

The desired compound was prepared according to the method of Example 36, except using methane sulfonyl chloride instead of benzene sulfonyl chloride.

NMR (CDCl$_3$, 300 MHz): δ 3.47-3.9 (c, 2H), 5.08 (bs, 0.5H), 5.6 (bs, 0.5H), 6.28 (s, 0.5H), 6.78 (bs, 0.5H), 7.22-7.25 (m, 1H), 7.3-7.45 (m, 2H), 7.54-7.61 (dd, 1H, J=7.4, J=1.8 Hz), 7.71-7.78 (m, 1H), 7.8-7.9 (m, 2H), 7.91-8.2 (c, 2H), 8.21-8.28 (d, 0.5H, J=7.4), 8.25 (d, 0.5H, J=7.4 Hz), 8.4-8.5 (m, 0.5H), 8.52-8.75 (m, 1.5H), 8.6-8.72 (m, 1H), 8.74-8.84 (m, 1H), 9.35 (bs, 1H).

EXAMPLE 38.

Preparation of
1-(N,N-Dimethylcarbamoyl)-3-[2-(3-pyridinyl)-thiazolid-4-oyl]indole The desired compound was prepared according to the method of Example 36, except using dimethyl carbamoyl chloride instead of benzene sulfonyl chloride.

NMR (CDCl$_3$, 300 MHz): δ 3.11 (s, 3H), 3.14 (s, 3H), 3.4-3.47 (m, 1H), 3.52-3.6 (m, 1H), 4.52-4.6 (t, 0.5H, J=7.4 Hz), 4.69-4.76 (m, 0.5H), 5.72 (s, 0.5H), 6.05 (s, 0.5H), 7.38-7.6 (m, 5H), 8.12-8.21 (m, 1H), 8.38-8.42 (m, 1H), 8.58 (d, 0.5H, J=5.5 Hz), 8.62 (dd, 0.5H, J=1.8, 5.5 Hz), 8.81 (d, 0.5H, J=1.8 Hz), 8.85 (dd, 0.5H, J=1.8, 5.5 Hz), 8.95 (bs, 0.5H), 9.1 (d, 0.5H, J=1.8 Hz).

EXAMPLE 39

Preparation of
2-Methyl-3-[2-(3-pyridinyl)-thiazolid-4-oyl]indole

The desired material was prepared using the method of Example 20, except using 2-methylindole instead of indole and methyl magnesium bromide instead of ethyl magnesium bromide.

NMR (CDCl$_3$, 300 MHz): δ 8.86 (d, 0.4 H, J=2.2), 8.81 (d, 0.6 H, J=1.9), 8.68 (bs, 1H (NH)), 8.62 (dd, 0.6 H, J=1.5, 4.8), 8.54 (dd, 0.4H, J=1.5, 4.4), 7.99 (m, 0.6H,), 7.92 (m, 0.4H), 7.72 (m, 1H), 7.34 (m, 3H), 7.24 (d, 0.6 H, J=3.3), 7.22 (d, 0.4 H, J=2.9), 6.07 (s, 0.4 H), 5.75 (s, 0.6 H), 4.92 (dd, 0.6 H, J=7.3, 8.4), 4.84 (t, 0.4H, J=7.4), 3.73 (dd, 0.6H, J=7.0, 11.8), 3.55 (dd, 0.4H, J=7.0, 10.6), 3.14 (dd, 0.6H, J=8.5, 10.7), 3.08 (dd, 0.4H, J=7.4, 10.7), 2.82 (s, 1.8H), 2.79 (s, 1.2H).

IR (KBr): 3440, 3280, 2920, 2840, 1630, 1455, 1420, 1170.

Mass Spectrum (FAB): 324[(M+1)$^+$, 12], 307 (10), 277 (10), 201 (20), 185.

EXAMPLE 40

Preparation of
1-tert-Butoxycarbonyl-2-methyl-3-[2-(3-pyridinyl)-thiazolid-4-oyl]indole oxalate The desired compound was prepared using the procedure of Example 28, except using 2-methyl-3-[2-(3-pyridinyl)-thiazolid-4-oyl]indole prepared as described in Example 39, instead of 3-[2-(3-pyridinyl)-thiazolid-4-oyl]indole. The oxalate salt was prepared as described in Example 3.

NMR (CDCl$_3$, 300 MHz): δ 8.85 (d, 0.4H, J=2.1), 8.81 (d, 0.6H, J=1.5), 8.62 (dd, 0.6H, J=1.5, 4.8), 8.55 (dd, 0.4H, J=2.1, 4.1), 8.12 (m, 1H), 7.98 (m, 0.6H), 7.86 (m, 0.4H), 7.32 (m, 4H), 6.00 (s, 0.4H), 5.52 (s, 0.6H), 4.90 (dd, 0.6H, J=7.0, 7.5), 4.83 (t, 0.4H, J=7.0), 3.53 (dd, 0.6H, J=7.0, 10.7), 3.40 (7.0, 10.7), 3.11 (m, 1H), 2.92 (s, 1.2H), 2.88 (s, 1.8H).

IR (CDCl$_3$): 3440, 2980, 2920, 1735, 1455, 1370, 1320, 1255, 1145, 1120.

Mass Spectrum (FAB): [424 (M+1)$^+$, 60], 154 (100).

EXAMPLE 41

Preparation of
1-Ethoxycarbonyl-3-[2-(3-pyridinyl)-thiazolid-4-oyl]indole oxalate The desired compound was prepared according to the method of Example 28, except using diethyl dicarbonate instead of ditert-butyl dicarbonate. The oxalate salt was prepared as described in Example 3.

NMR (CDCl$_3$, 300 MHz): δ 8.84 (d, 0.5H, J=1.2), 8.80 (d, 0.5H, J=1.3), 8.61 (dd, 0.5H, J=1.2, 4.3), 8.54 (dd, 0.5H, J=1.3, 4.5), 8.42 (s, 0.5H), 8.39 (m, 1H), 8.35 (s, 0.5H), 8.21 (bds, 0.5H, (NH)), 8.19 (bds, 0.5H, (NH)), 7.95 (m, 0.5H), 7.88 (m, 0.5H), 7.40 (m, 4H), 6.01 (bds, 0.5H), 5.73 (m, 0.5H), 4.70 (m, 1H), 4.16 (s, 1.5H), 4.12 (s, 1.5H), 3.57 (dd, 0.5H, J=7.4, 10.6), 3.43 (dd, 0.5H, J=7.4, 10.3), 3.17 (m, 1H).

IR (CDCl$_3$): 3480, 3300, 3030, 2980, 2920, 1755, 1665, 1540, 1450, 1440, 1235.

Mass Spectrum (FAB): 368 [(M+1)+, 20], 201 (20), 185 (100).

EXAMPLE 42

Preparation of 1-Methoxycarbonyl-3-[2-(3-pyridinyl)-thiazolid-4-oyl]indole oxalate The desired compound was prepared according to the method of Example 28, except using dimethyldicarbonate instead of ditert-butyl dicarbonate. The oxalate salt was prepared as described in Example 3.

NMR (CDCl$_3$, 300 MHz): δ 8.84 (d, 0.5H, J=1,2), 8.80 (d, 0.5H, J=1.3), 8.61 (dd, 0.5H, J =1.2, 4.3), 8.54 (dd, 0.5H, J=1.3, 4.5), 8.42 (s, 0.5H), 8.39 (m, 1H), 8.35 (s, 0.5H), 8.21 (bds, 0.5H, (NH)), 8.19 (bds, 0.5H, (NH)), 7.95 (m, 0.5H), 7.88 (m, 0.5H), 7.40 (m, 4H), 6.01 (bds, 0.5H), 5.73 (m, 0.5H), 4.70 (m, 1H), 4.16 (s, 1.5H), 4.12 (s, 1.5H), 3.57 (dd, 0.5H, J=7.4, 10.6), 3.43 (dd, 0.5H, J=7.4, 10.3), 3.17 (m, 1H).

IR (CDCl$_3$): 3480, 3300, 3030, 2980, 2920, 1755, 1665, 1540.

Mass Spectrum (FAB): 368 [(M+1)+, 20], 201 (20), 185 (100).

EXAMPLE 43

Preparation of 1-iso-Propylsulfonyl-3-[2-(3-pyridinyl)-thiazolid-4-oyl]indole

The desired compound was prepared according to the method of Example 36, except using iso-propyl sulfonyl chloride instead of benzene sulfonyl chloride.

NMR (CDCl$_3$, 300 MHz): δ 1.3–1.45 (6H), 3.16–3.68 (3H), 4.6–4.75 (1H), 5.72 (1H, 5), 7.31–7.34 (2H), 7.45–7.5 (2H), 7.86–7.92 (2H), 8.4–8.49 (1H), 8.53–8.6 (1H), 8.61–8.62 (1H), 8.79–8.5 (1H).

Mass Spectrum (DCI/NH$_3$): 416 (M+H)+, 310, 320

EXAMPLE 44

Preparation of 1-(4-Chlorobenzoyl)-3-[2-(3-pyridinyl)-thiazolid-4-oyl]indole

The desired compound was prepared according to the method of Example 36, except using 4-chlorobenzoyl chloride instead of benzene sulfonyl chloride.

Melting Point 80°–84° C.

NMR (CDCl$_3$, 300 MHz): d 3.15–3.5 (2H), 4.51–4.63 (1H), 5.69 (0.5H), 5.93 (0.5H), 7.44–7.51 (3H), 7.52–7.65 (3H), 7.69–7.78 (3H), 7.81–7.85 (0.5H), 7.91–7.95 (0.5), 8.16–8.22 (1H), 8.39–8.45 (1H), 8.51–8.55 (0.5H), 8.6–8.65 (0.5H), 8.75–8.81 (1H).

Mass Spectrum (DCI/NH$_3$): 448 (M+H)+, 310.

EXAMPLE 45

Preparation of 1-Phenylmethoxycarbonyl-3-[2-(3-pyridinyl)-thiazolid-4-oyl]indole oxalate The desired compound was prepared according to the method of Example 36, except using benzyl chloroformate instead of benzene sulfonyl chloride. The oxalate salt was prepared as described in Example 3.

NMR (CDCl$_3$, 300 MHz): δ 8.82 (d, 0.5H, J=1.4), 8.79 (d, 0.5H, J=2.2), 8.61 (dd, 0.5H, J=1.9, 4.8), 8.54 (dd, 0.5H, J=1.1, 4.8), 8.40 (s, 0.5H), 8.38 (m, 1H), 8.35 (s, 0.5H), 8.18 (m, 1H), 7.95 (m, 0.5H), 7.87 (m, 0.5H), 7.45 (m, 8H), 5.99 (d, 0.5H, J=8.0), 5.72 (d, J=12.9), 5.55 (bs, 1H), 5.51 (bs, 1H), 4.71 (m, 0.5H), 4.66 (m, 0.5H), 3.55 (dd, 0.5H, J=7.3, 10.2), 3.40 (dd, 0.5H, J=7.0, 10.3), 3.18 (dd, 0.5H, J=4.4, 10.8), 3.14 (dd, 0.5H, J=3.0, 7.8).

IR (CDCl$_3$): 3480, 3300, 3040, 2960, 2900, 1740, 1670, 1540, 1450, 1225.

Mass Spectrum (DCI/NH$_3$): 444 [(M+1)+, 100], 410 (25), 324 (25), 310 (50).

EXAMPLE 46

Preparation of 1-Phenylmethyl-3-[2-(3-pyridinyl)-thiazolid-4-oyl]indole

The desired compound was prepared according to the method of Example 36, except using benzylchloride instead of benzene sulfonyl chloride, and using potassium hexamethyl disilazide in tetrahydrofuran instead of potassium hydroxide in dimethoxyethane.

NMR (CDCl$_3$, 300 MHz): δ 3.0–3.25 (2H), 4.81–4.89 (1H), 5.5 (2H), 5.98 (1H), 7.21–7.26 (4H), 7.31–7.35 (3H), 7.53–7.6 (1H), 7.82–7.91 (1H), 8.21–8.26 (1H), 8.45–8.49 (1H), 8.55–8.58 (1H), 8.67 (1H), 8.75 (1H), 8.9 (1H).

Mass Spectrum (DCI/NH$_3$): 400 (M+H)+, 401, 198, 108.

EXAMPLE 47

Preparation of 1-tert-Butoyl-3-[2-(3-pyridinyl)-thiazolid-4-oxyl]indole

The desired compound was prepared according to the method of Example 36, except using ethyl chloroformate instead of benzene sulfonyl chloride, and using potassium hexamethyl disilazide in tetrahydrofuran instead of potassium hydroxide in dimethoxyethane.

Melting Point: 78°–80° C.

NMR (CDCl$_3$, 300 MHz): δ 1.22 (9H), 3.21–3.6 (2H), 4.62–4.75 (1H), 5.78 (1H), 7.39–7.48 (3H), 7.95–8.01 (1H), 8.32–8.38 (1H), 8.42–8.49 (1H), 8.55 (1H), 8.6 (1H), 8.8 (0.5H), 8.89 (0.5H), 9.1 (0.5H), 9.21 (0.5H).

Mass Spectrum (DCI/NH$_3$): 394(M+H)+, 310, 119.

EXAMPLE 48

Preparation of 1-(N,N-Diethylcarbamoyl)-3-[2-(3-pyridinyl)-thiazolid-4-oyl]indole The desired compound was prepared according to the method of Example 36, except using diethyl carbamoyl chloride instead of benzene sulfonyl chloride, and using sodium hydride in tetrahydrofuran instead of potassium hydroxide in dimethoxyethane. Melting point: 84° C. NMR (CDCl$_3$, 300 MHz): δ 1.2–1.31 (6H), 3.1–3.29 (2H), 3.4–3.51 (4H), 4.5–4.58 (1H), 6.32–6.5 (1H), 7.35–7.42 (2H), 7.49–7.52 (1H), 7.7–7.77 (1H), 8.1–8.12 (1H), 8.16–8.2 (1H), 8.35–8.4 (2H), 8.61–8.68 (0.5H), 8.82–8.89 (0.5H), 9–9.02 (0.5H) 9.09–9.1 (0.5H).

Mass Spectrum (DCI/NH$_3$): 409(M+H)+, 410,107.

EXAMPLE 49

Preparation of 1-(N-Methyl, N-Phenyl)-3-[2-(3-pyridinyl)-thiazolid-4-oyl]indole

The desired compound was prepared according to the method of Example 36, except using N-methyl N-phenyl carbamoyl chloride instead of benzene sulfonyl chloride, and using sodium hydride in tetrahydrofuran instead of potassium hydroxide in dimethoxyethane.

Melting Point: 72°-76° C. NMR (CDCl$_3$, 300 MHz): δ 2.6-2.9 (2H), 3.62, 4.07-4.3. (1H), 5.61-6 (1H), 7.1-7.6 (9H), 7.98-8.3 (2H), 8.22-8.32 (2H), 8.6-8.65 (1H), 8.9 (0.5H),.9.1 (0.5H). Mass Spectrum (DCI/NH$_3$): 443 (M+H)+, 310, 311, 107.

EXAMPLE 50.

Preparation of 7-Phenylmethoxy-3-[2-(3-pyridinyl)-thiazolid-4-oyl]indole

The desired material was prepared using the method of Example 20, except using 6-phenylmethoxy indole instead of indole and methyl magnesium bromide instead of ethyl magnesium bromide.

NMR (DMSO-d$_6$, 300 MHz): δ 12.4 (bd, 0.6H, NH), 12.3 (bd, 0.4H, NH), 8.75 (d, 0.6H, J=2.2), 8.67 (d, 0.4H, J=2.5), 8.57 (dd, 0.6H, J=1.4, 4.8), 8.51 (m, 1H), 8.46 (dd, 0.4H, J=1.4, 4.4), 8.03 (dt, 0.6H, J=2.1, 8.1), 7.88 (m, 0.4H), 7.80 (d, 0.4H, J=7.6), 7.79 (d, 0.6H, J=7.6), 7.58 (d, 2H, J=8.0), 7.42 (m, 4H), 7.13 (m, 1H), 6.93 (d, 0.6H, J=3.3), 6.91 (d, 0.4H, J=3.4), 5.97 (s, 0.6H), 5.69 (s, 0.4H), 5.31 (s, 1.2H), 5.30 (s, 0.4H), 4.90 (t, 0.6H, J=7.0), 4.83 (m, 0.4H), 3.55 (dd, 0.6H, J=7.6, 10.0), 3.48 (dd, 0.4H, J=7.0, 9.9), 3.06 (dd, 0.6H, J=9.5, 9.2), 3.00 (dd, 0.4H, J=6.9, 9.9).

Mass Spectrum (DCI/NH$_3$): 416 [(M+1)+, 80], 382 (25), 293 (100), 225 (85), 124.

EXAMPLE 51

Preparation of 1-(N,N-Dimethylcarbamoyl)-7-phenylmethoxy-3-[2-(3-pyridinyl)-thiazolid-4-oyl]indole The desired compound is prepared according to the method of Example 36, except using N,N-dimethyl carbamoyl chloride instead of benzene sulfonyl chloride and using 7-phenylmethoxy-3-[2-(3-pyridinyl)-3-tert-butoxycarbonylthiazolid-4-oyl]indole instead of 3-[2-(3-pyridinyl)-3-tert-butoxycarbonylthiazolid-4-oyl]indole.

EXAMPLE 52

Preparation of 1-(N,N-Dimethylcarbamoyl)-6-phenylmethoxy-3-[2-(3-pyridinyl)-thiazolid-4-oyl]indole The desired compound is prepared according to the method of Example 36, except using N,N-dimethyl carbamoyl chloride instead of benzene sulfonyl chloride and using 6-phenylmethoxy-3-[2-(3-pyridinyl)-3-tert-butoxycarbonylthiazolid-4-oyl]indole instead of 3-[2-(3-pyridinyl)-3-tert-butoxycarbonylthiazolid-4-oyl]indole.

EXAMPLE 53

Preparation of 1-tert-Butoxycarbonyl-7-phenylmethoxy-3-[2-(3-pyridinyl)-thiazolid-4-oyl]indole The desired compound is prepared using the procedure of Example 28, except using 7-phenylmethoxy-3-[2-(3-pyridinyl)-thiazolid-4-oyl]indole prepared as described in Example 33, instead of 3-[2-(3-pyridinyl)-thiazolid-4-oyl]indole.

EXAMPLE 54

Preparation of 1-(N-tert-Butoxycarbamoyl)-3-[2-(3-pyridinyl)-thiazolid-4-oyl]indole The desired compound is prepared according to the method of Example 36, except using N-tert-butylisocyanate instead of benzene sulfonyl chloride.

EXAMPLE 55

Preparation of 1-(1-Morpholinocarbonyl)-3-[2-(3-pyridinyl)-thiazolid-4-oyl]indole The desired compound is prepared according to the method of Example 36, except using N-morpholino carbonylchloride instead of benzene sulfonyl chloride.

EXAMPLE 56

Preparation of 1-tert-Butoxycarbonyl-3-[2-(3-pyridinyl)-3-formylcarbonylthiazolid-4-oyl]indole Triethylamine (0.346 mL, 2.5 mmol) and aceticformic anhydride (0.146 g, 1.67 mmol) was added to a solution of 1-tert-butoxycarbonyl-3-[2-(3-pyridinyl)-thiazolid-4-oyl]indole, prepared as described in Example 28 (0.34 g, 0.831 mmol) in THF (40 mL). The mixture was stirred for 5 hour and then saturated aqueous ammonium chloride was added. The resulting mixture was extracted with ethyl acetate and the organic washed twice with saturated aqueous sodium chloride and dried over magnesium chloride. The solvent was removed in vacuo and the residue chromatographed on silica gel eluting with ethyl acetate:hexanes (3:2) to afford the desired compound as a white solid (0.27 g, 74%). Melting Point 125°-130° C.; NMR (CDCl$_3$, 300 MHz): δ 1.74 (s, 9H), 3.35 (m, 1H), 3.5 (m, 1H), 3.65 (m, 1H), 5.68 (m, 1H), 6.18 (s, 0.5H), 6.23 (s, 0.5H), 7.4 (m, 4H), 8.15 (m, 1H), 8.35 (m, 2H), 8.49 (d, 1H), 8.60 (m, 1H).; IR (CDCl$_3$): 1660 C=O Mass Spectrum (DCI/NH$_3$): 438 (M+H)+.

EXAMPLE 57

Preparation of 1-tert-Butoxycarbonyl-3-[2-(3-pyridinyl)-3-acetyl-thiazolid-4-oyl]indole The desired compound was prepared according to the method of Example 56, except using acetic anhydride instead of aceticformic anhydride.

Melting Point: 170°-173° C.; NMR (CDCl$_3$, 300 MHz): δ 1.75 (s, 9H), 2.03 (s, 3H), 3.33 (m, 2H), 5.65 (m, 1H), 7.45 (m, 4H), 8.15 (m, 1H), 8.42 (m, 1H), 8.50 (s, 1H), 8.63 (m, 3H), 8.88 (bs, 1H). Mass Spectrum (DCI/NH$_3$): 452 (M+H)+

EXAMPLE 58

Preparation of 1-tert-Butoxycarbonyl-3-[2-(3-pyridinyl)-3-acetyl-thiazolid-4-oyl]indole The desired compound was prepared according to the method of Example 56, except using trimethylsilylisocyanate instead of aceticformic anhydride.

Melting Point: 141°-143° C.

NMR (CDCl$_3$, 300 MHz): δ 1.72 (s, 9H), 3.28 (m, 1H), 3.44 (m, 1H), 4.4 (bs, 1H), 5.65 (m, 0.25H), 5.73 (m, 0.75H), 6.09 (s, 0.75H), 6.19 (s, 0.25H), 7.4 (m, 4H), 8.15

What is claimed is:

1. A compound having the structure:

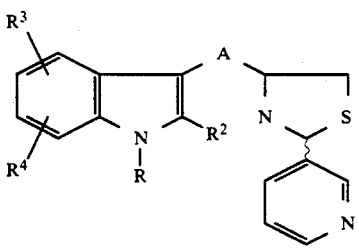

or a pharmaceutically acceptable salt thereof where A is methylene or carbonyl;

R is selected from the group consisting of
  hydrogen,
  alkyl of from one to six carbon atoms,
  phenylalkyl in which the alkyl portion contains from one to four carbon atoms,
  —C(O)NR⁶R⁷ where R⁶ and R⁷ are independently hydrogen or alkyl of from one to six carbon atoms,
  —C(O)OR⁸ where R⁸ is selected from
    alkyl of from one to six carbon atoms,
    phenyl, optionally substituted with alkyl of from one to six carbon atoms, alkoxy of from one to six carbon atoms, or halogen,
    phenylalkyl in which the alkyl portion contains from one to four carbon atoms,
    phenylalkyl as previously defined optionally substituted with alkyl of from one to six carbon atoms, alkoxy of from one to six carbon atoms, or halogen;
  —C(O)R⁹ where R⁹ is hydrogen or alkyl of from one to six carbon atoms, and
  benzoyl, optionally substituted with alkyl of from one to six carbon atoms, alkoxy of from one to six carbon atoms, or halogen;

R² is selected from hydrogen or alkyl of from one to six carbon atoms;

R³ and R⁴ are independently selected from the group consisting of
  (a) hydrogen,
  (b) halogen,
  (c) alkyl of from one to six carbon atoms,
  (d) alkoxy of from one to six carbon atoms,
  (e) alkoyl of from one to six carbon atoms,
  (f) cyano,
  (g) phenylalkoxy in which the alkoxy portion contains from one to six carbon atoms,
  (h) phenoxy, and
  (i) benzoyl, optionally substituted with alkyl of from one to six carbon atoms, alkoxy of from one to six carbon atoms, or halogen.

2. A compound as defined by claim 1 wherein A is carbonyl.

3. A compound as defined by claim 2 wherein R² is hydrogen; R is selected from hydrogen, —C(O)NR⁶R⁷ where R⁶ and R⁷ are as defined therein, C(O)OR⁸ where R⁸ is as defined therein, or phenylalkyl in which the alkyl portion contains from one to six carbon atoms; R³ is selected from hydrogen, alkyl of from one to six carbon atoms, and phenylalkoxy in which the alkoxy portion contains from one to six carbon atoms; and R⁴ is hydrogen; or a pharmaceutically acceptable salt thereof.

4. A compound as defined by claim 3 wherein R is hydrogen, methyl, ethyl, —C(O)N(CH₃)₂, —C(O)N(CH₂CH₃)₂, and tert-butoxycarbonyl; R³ is selected from hydrogen, phenylmethoxy, and methyl; R² and R⁴ are hydrogen; X is NH, and Y is S, or a pharmaceutically acceptable salt thereof.

5. A compound as defined by claim 1 selected from the group consisting of
3-[2-(3-pyridinyl)-thiazolid-4-ylmethyl]indole;
3-[2-(3-pyridinyl)-thiazolid-4-oyl]indole;
1-methyl-3-[2-(3-pyridinyl)-thiazolid-4-oyl]indole;
2-methyl-3-[2-(3-pyridinyl)-thiazolid-4-oyl]indole;
7-methyl-3-[2-(3-pyridinyl)thiazolid-4-oyl]indole;
1,2-dimethyl-3-[2-(3-pyridinyl)-thiazolid-4-oyl]indole;
1-ethyl-3-[2-(3-pyridinyl)-thiazolid-4-oyl]indole;
1pivaloyl-3-[2-(3-pyridinyl)-thiazolid-4-oyl]indole (?)
1-phenylmethyl-3-[2-(3-pyridinyl)-thiazolid-4-oyl]indole;
3-[2-(3-pyridinyl)thiazolid-4-oyl]-4-phenylmethoxyindole;
3-[2-(3-pyridinyl)thiazolid-4-oyl]-5-phenylmethoxyindole;
3-[2-(3-pyridinyl)thiazolid-4-oyl]-6-phenylmethoxyindole;
3-[2-(3-pyridinyl)thiazolid-4-oyl]-7-phenylmethoxyindole;
1-methylsulfonyl-3-[2-(3-pyridinyl)-thiazolid-4-oyl]indole;
1-iso-propylsulfonyl-3-[2-(3-pyridinyl)-thiazolid-4-oyl]indole;
1-phenylsulfonyl-3-[2-(3-pyridinyl)-thiazolid-4-oyl]indole;
1-(4-chlorobenzoyl)-3-[2-(3-pyridinyl)-thiazolid-4-oyl]indole;
1-tert-butoxycarbonyl-3-[2-(3-pyridinyl)-thiazolid-4-oyl]indole;
1-tert-butoxycarbonyl-6-phenylmethoxy-3-[2-(3-pyridinyl)-thiazolid-4-oyl]indole;
1-tert-butoxycarbonyl-2-methyl-3-[2-(3-pyridinyl)-thiazolid-4-oyl]indole;
1-ethoxycarbonyl-3-[2-(3-pyridinyl)-thiazolid-4-oyl]indole;
1-methoxycarbonyl-3-[2-(3-pyridinyl)-thiazolid-4-oyl]indole;
1-tert-butoxycarbonyl-7-phenylmethoxy-3-[2-(3-pyridinyl)-thiazolid-4-oyl]indole;
1-tert-butoxycarbonyl-3-[2-(3-pyridinyl)-3-formylcarbonylthiazolid-4-oyl]indole;
1-tert-butoxycarbonyl-3-[2-(3-pyridinyl)-3-acetyl-thiazolid-4-oyl]indole;
1-tert-butoxycarbonyl-3-[2-(3-pyridinyl)-3-acetyl-thiazolid-4-oyl]indole;
1-phenylmethoxycarbonyl-3-[2-(3-pyridinyl)-thiazolid-4-oyl]indole;
1-(N,N-dimethylcarbamoyl)-3-[2-(3-pyridinyl)-thiazolid-4-oyl]indole;
1-(N,N-diethylcarbamoyl)-3-[2-(3-pyridinyl)-thiazolid-4-oyl]indole;
1-(N,N-dimethylcarbamoyl)-7-phenylmethoxy-3-[2-(3-pyridinyl)-thiazolid-4-oyl]indole;
1-(N,N-dimethylcarbamoyl)-6-phenylmethoxy-3-[2-(3-pyridinyl)-thiazolid-4-oyl]indole;
1-(N-tert-butoxycarbamoyl)-3-[2-(3-pyridinyl)-thiazolid-4-oyl]indole;
1-(1-morpholinocarbonyl)-3-[2-(3-pyridinyl)-thiazolid-4-oyl]indole;

1-[2-(3-pyridinyl)-dithiolan-4-oyl]indole;
3-[2-(3-pyridinyl)-dithiolan-4-oyl]indole;
1-phenylsulfonyl 3-[2-(3-pyridinyl)-dithiolan-4-oyl]indole;
cis-1-tert-butoxycarbonyl-3-[2-(3-pyridinyl)-dithiolan-4-oyl]indole;
trans-1-tert-butoxycarbonyl-3-[2-(3-pyridinyl)-dithiolan-4-oyl]indole;
1-(N-methyl, N-phenylcarbamoyl)-3-[2-(3-pyridinyl)-thiazolid-4-oyl]indole;
or a pharmaceutically acceptable salt thereof.

6. A pharmaceutical composition useful for inhibiting PAF in a mammal in need of such treatment comprising a PAF-inhibitive effective amount of a compound as defined by claim 1 in combination with a pharmaceutically acceptable carrier.

7. A method of inhibiting PAF activity in a mammal in need of such treatment comprising administering a PAF-inhibitive effective amount of a compound as defined by claim 1.

8. A method of treating PAF-mediated disorders comprising administering to a mammel in need of such treatment a therapeutically effective amount of a compound as defined by claim 1.

* * * * *

UNITED STATES PATENT AND TRADEMARK OFFICE
CERTIFICATE OF CORRECTION

PATENT NO. : 5,120,749

DATED : June 9, 1992

INVENTOR(S) : James B. Summers; George S. Sheppard; James G. Phillips; Daisy Pireh; Douglas H. Steinman; Paul D. May.

It is certified that error appears in the above-identified patent and that said Letters Patent is hereby corrected as shown below:

COLUMN 47, LINES 6-17:

Please correct the chemical structure indicated in Claim 1 by deleting the structure

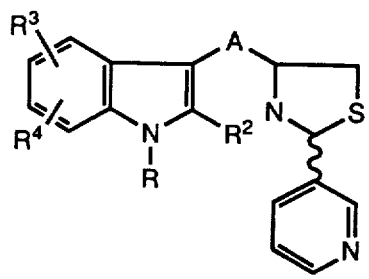

and inserting in place thereof the structure

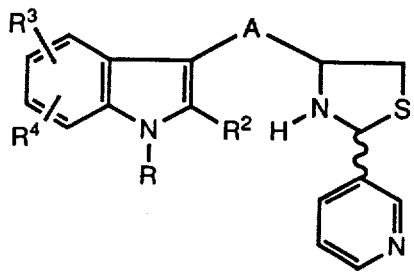

UNITED STATES PATENT AND TRADEMARK OFFICE
CERTIFICATE OF CORRECTION

PATENT NO. : 5,120,749

DATED : June 9, 1992

INVENTOR(S) : James B. Summers, et al

It is certified that error appears in the above-identified patent and that said Letters Patent is hereby corrected as shown below:

COLUMN 48, LINE 7: Delete the phrase "X is NH and Y is S". The phrase is redundant since the generic structure of Claim 1 requires that X be NH and y be sulfur.

Signed and Sealed this

Third Day of August, 1993

*Attest:*

MICHAEL K. KIRK

*Attesting Officer*  *Acting Commissioner of Patents and Trademarks*